US011844786B2

(12) United States Patent
Duffield et al.

(10) Patent No.: US 11,844,786 B2
(45) Date of Patent: *Dec. 19, 2023

(54) USES OF COMBINATIONS (+)-α-DIHYDROTETRABENAZINE AND (−)-α-DIHYDROTETRABENAZINE IN METHODS OF TREATING MOVEMENT DISORDER

(71) Applicant: ADEPTIO PHARMACEUTICALS LIMITED, London (GB)

(72) Inventors: Andrew John Duffield, Berkhamsted (GB); Anant Pandya, Croydon (GB)

(73) Assignee: ADEPTIO PHARMACEUTICALS LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/939,828

(22) Filed: Mar. 29, 2018

(65) Prior Publication Data

US 2018/0280359 A1    Oct. 4, 2018

Related U.S. Application Data

(60) Provisional application No. 62/515,930, filed on Jun. 6, 2017.

(30) Foreign Application Priority Data

Apr. 1, 2017    (GB) .................................... 1705304

(51) Int. Cl.
*A61K 31/4375*   (2006.01)
*A61P 25/14*     (2006.01)
*A61K 31/435*    (2006.01)

(52) U.S. Cl.
CPC ............ *A61K 31/435* (2013.01); *A61P 25/14* (2018.01); *A61K 2300/00* (2013.01)

(58) Field of Classification Search
CPC .... A61P 25/14; A61K 31/473; A61K 31/4375
See application file for complete search history.

(56) References Cited

U.S. PATENT DOCUMENTS

| 7,919,622 | B2 | 4/2011 | Amarasinghe et al. | |
|---|---|---|---|---|
| 8,039,627 | B2 | 10/2011 | Gano | |
| 2010/0087475 | A1 | 4/2010 | Duffield et al. | |
| 2012/0003330 | A1* | 1/2012 | Gant .................... | C07D 471/04 424/722 |
| 2018/0280360 | A1 | 10/2018 | Duffield et al. | |
| 2018/0280361 | A1 | 10/2018 | Duffield et al. | |
| 2018/0280374 | A1 | 10/2018 | Duffield et al. | |
| 2018/0280375 | A1 | 10/2018 | Duffield et al. | |
| 2019/0111035 | A1 | 4/2019 | Duffield et al. | |

FOREIGN PATENT DOCUMENTS

| CN | 102285984 | * | 12/2011 |
|---|---|---|---|
| GB | 800969 A | | 9/1958 |
| WO | 2005077946 A1 | | 8/2005 |
| WO | 2006053067 A2 | | 5/2006 |
| WO | 2007007105 A1 | | 1/2007 |
| WO | 2007017654 A1 | | 2/2007 |
| WO | 2008058261 A1 | | 5/2008 |
| WO | 2009073677 A1 | | 6/2009 |
| WO | 2010018408 A2 | | 2/2010 |
| WO | 2010026436 A2 | | 3/2010 |
| WO | 2011153157 A2 | | 12/2011 |
| WO | 2014047167 A1 | | 3/2014 |
| WO | 2015120110 A2 | | 8/2015 |
| WO | 2015171802 A1 | | 11/2015 |
| WO | 2016127133 A1 | | 8/2016 |
| WO | 2016210180 A2 | | 12/2016 |
| WO | 2017112857 A1 | | 6/2017 |
| WO | 2018140092 A1 | | 8/2018 |
| WO | 2018140093 A1 | | 8/2018 |
| WO | 2018140094 A1 | | 8/2018 |
| WO | 2018140095 A2 | | 8/2018 |
| WO | 2018140096 A1 | | 8/2018 |

OTHER PUBLICATIONS

Rishel et al (J Org Chem, 2009; 74:4001-4004) (Year: 2009).*
Muller (Expert opinion on investigational drugs, 2015; 24(6):737-742) (Year: 2015).*
"Archive History for NCT02844179 (+)-Alpha-Dihydrotetrabenazine Phase I" U.S. National Library of Medicine, https://clinicaltrials.gov/ct2/history/NCT02844179?V_1=View#StudyPageTop (2016).
Kilbourn, "Rat pancreas uptake of [11C]dihydrotetrabenazine stereoisomers" Nucl. Med. Biol. (2010), 37(8), pp. 869-871.
Boldt et al., "Synthesis of (+)- and (−)Tetrabenazine from the Resolution of [alpha]-Dihydrotetrabenazine", Synth. Commun., (2009), 39(20), pp. 3574-3585.
Yao, et al., "Preparation and Evaluation of Tetrabenazine Enantiomers and All Eight Stereoisomers of Dihydrotetrabenazine as VMAT2 Inhibitors", Eur. J. Med. Chem., 46, pp. 1841-1848, (2011).
Kilbourn, et al., "Binding of α-dihydrotetrabenazine to the Vesicular Monoamine Transporter is Stereospecific", Eur. J. Pharmacol., 278(3), pp. 249-252, (1995).
Bhatnagar, et al., "Pharmacokinetics of Dihydrotetrabenazine After Intravenous and Peroral Administration to Rats", Pharm Pharmacol Lett, 2(3), pp. 89-91, (1992).
Mehvar, et al., "Pharmacokinetics of Tetrabenazine and its Major Metabolite in Man and Rat", Drug Metab. Dispos., 15(2), pp. 250-255, (1987).
Roberts, et al., "The Pharmacokinetics of Tetrabenazine and its Hydroxy Metabolite in Patients Treated for Involuntary Movement Disorders", Eur. J. Clin. Pharmacol., 29, pp. 703-708., (1986).
Kilbourn, et al., "Absolute Configuration of (+)-α-Dihydrotetrabenazine, an Active Metabolite of Tetrabenazine", Chirality, 9, pp. 59-62, (1997).

(Continued)

*Primary Examiner* — Rayna Rodriguez
(74) *Attorney, Agent, or Firm* — Heslin Rothenberg Farley & Mesiti P.C.

(57) ABSTRACT

The invention relates to pharmaceutical compositions containing both (+)-α-dihydrotetrabenazine and (−)-α-dihydrotetrabenazine and their therapeutic uses, for example in the treatment of movement disorders, such as Tourette's syndrome.

21 Claims, 4 Drawing Sheets

(56) References Cited

OTHER PUBLICATIONS

Brossi, et al., "Syntheseversuche in der Emetin-Reihe, 3. Mitteilung", Helv. Chim Acta., vol. XLI, No. 193, pp. 1793-1806, (1958) (and English Translation).
Schwartz, et al, "Metabolic Studies of Tetrabenazine, A Psychotropic Drug in Animals and Man", Biochem. Pharmacol., 15, pp. 645-655, (1956).
Scherman, et al., "Hydrophobicity of the Tetrabenazine-Binding Site of the Chromaffin Granule Monoamine Transporter", Mol. Pharmacol., 33, pp. 72-77, (1987).
Mehvar, et al., "Concentration-Effect Relationships of Tetrabenazine and Dihydrotetrabenazine in the Rat", J. Pharm. Sci., 76(6), pp. 461-465, (1987).
Kilbourn, "PET Radioligands for Vesicular Neurotransmitter Transporters", Med. Chem. Res., 5, pp. 113-126, (1994).
Kilbourn, et al., "In Vivo Measures of Dopaminergic Radioligands in the Rat Brain: Equilibrium Infusion Studies", Synapse, 43, pp. 188-194, (2002).
Müller, "Valbenazine Granted Breakthrough Drug Status for Treating Tardive Dyskinesia", Expert Opin. Investig. Drugs, 24(6), pp. 737-742, (2015).
Hauser, et al., "KINECT 3: A Randomised, Double-Blind Placebo-Controlled Phase 3 Trial of Valbenazine (NBI-98854) for Tardive Dyskinesia (PL02.003)", Neurology, (2016), 86(16 Supplement). Abstract.
Hauser, et al., "KINECT 3: A Phase 3 Randomised, Double-Blind, Placebo-Controlled Trial of Valbenazine for Tardive Dyskinesia", Am. J. Psychiatry, 174(5), pp. 476-484, (2017).
Ashcroft, et al., "A Comparison of Tetrabenazine and Chlorpromazine in Chronic Schizophrenia", Br. J. Psychiatry, 107(447), pp. 287-293, (1961).
Chen, et al. "Tetrabenazine for the Treatment of Hyperkinetic Movement Disorders: A Review of the Literature", Clin. Ther., 34(7), pp. 1487-1504, (2012).
Shen, et al., "Safety and Efficacy of Tetrabenazine and Use of Concomitant Medications During Long-Term, Open-Label Treatment of Chorea Associated with Huntington's and Other Diseases", Tremor Other Hyperkinet Mov, 3, pp. 1-13., (2013).
Skor, et al., "Differences in Dihydrotetrabenazine Isomer Concentrations Following Administration of Tetrabenazine and Valbenazine", Drugs R&D, 17(3), pp. 449-459, (2017).
Duffield, et al., "Pharmaceutical Compositions", U.S. Appl. No. 15/939,826, filed Mar. 29, 2018, pp. 1-74.
Duffield, et al., "Pharmaceutical Compositions", U.S. Appl. No. 15/939,831, filed Mar. 29, 2018, pp. 1-42.
Duffield, et al., "Pharmaceutical Compositions", U.S. Appl. No. 15/939,837, filed Mar. 29, 2018, pp. 1-53.
Duffield, et al., "Pharmaceutical Compositions", U.S. Appl. No. 15/939,822, filed Mar. 29, 2018, pp. 1-71.
Walkup, J.T., "A Guide to Tourette Syndrome Medications", https://depts.washington.edu/dbpeds/A%20Guide%20to%20TS%20Medications_M-313.pdf, pp. 1-14 (2008).

* cited by examiner

USES OF COMBINATIONS (+)-α-DIHYDROTETRABENAZINE AND (−)-α-DIHYDROTETRABENAZINE IN METHODS OF TREATING MOVEMENT DISORDER

CROSS REFERENCE TO RELATED APPLICATIONS

This application claims priority to U.S. Provisional Application No. 62/515,930, filed on Jun. 6, 2017, and to Great Britain Application No. 1705304.2, filed on Apr. 1, 2017. The entire contents of each of the prior applications are hereby incorporated herein by reference.

This invention relates to pharmaceutical compositions containing both (+)-α-dihydrotetrabenazine and (−)-α-dihydrotetrabenazine and their therapeutic uses, for example in the treatment of movement disorders, such as Tourette's syndrome.

BACKGROUND OF THE INVENTION

Movement disorders can generally be classified into two categories: hyperkinetic movement disorders and hypokinetic movement disorders. Hyperkinetic movement disorders are caused by an increase in muscular activity and can cause abnormal and/or excessive movements, including tremors, dystonia, chorea, tics, myoclonus and stereotypies.

Hyperkinetic movement disorders often are often psychological in nature and arise through improper regulation of amine neurotransmitters in the basal ganglia.

A particular hyperkinetic movement disorder is Tourette's syndrome, which is an inherited neurological condition characterised by multiple physical and vocal tics. The tics are usually repetitive, but random, physical movements or vocal noises.

The vocal tics can be of various forms and include repeating one's own words, the words of others or other sounds. Onset usually occurs in children and continues through to adolescence and adulthood.

While the tics associated with Tourette's syndrome are temporarily suppressible, those affected can usually only suppress their tics for limited time periods. There is yet to be an effective treatment to cover all types of tics in all patients, but certain medicaments for tic suppression have been developed.

It is known that dopamine receptor antagonists display an ability to supress tics in Tourette's syndrome patients and a number dopamine receptor antagonists are currently used in the suppression of Tourette's tics, such as fluphenazine, haloperidol and pimozide.

Type 2 vesicular monoamine transporter (VMAT2) is a membrane protein responsible for the transportation of monoamine neurotransmitters, such as dopamine, serotonin and histamine, from cellular cytosol into synaptic vesicles. Inhibition of this protein hinders presynaptic neurons from releasing dopamine, resulting in a depletion of dopamine levels in the brain.

VMAT2 inhibitors can be used to treat the symptoms of Tourette's syndrome.

Tetrabenazine (Chemical name: 1,3,4,6,7,11b-hexahydro-9,10-dimethoxy-3-(2-methylpropyl)-2H-benzo(a)quinolizin-2-one) has been in use as a pharmaceutical drug since the late 1950s. Initially used as an anti-psychotic, tetrabenazine is currently used for treating hyperkinetic movement disorders such as Huntington's disease, hemiballismus, senile chorea, tic, tardive dyskinesia and Tourette's syndrome, see for example Jankovic et al., *Am. J. Psychiatry.* (1999) August; 156(8):1279-81 and Jankovic et al., *Neurology* (1997) February; 48(2):358-62.

The primary pharmacological action of tetrabenazine is to reduce the supply of monoamines (e.g. dopamine, serotonin, and norepinephrine) in the central nervous system by inhibiting the human vesicular monoamine transporter isoform 2 (hVMAT2). The drug also blocks post-synaptic dopamine receptors.

The central effects of tetrabenazine closely resemble those of reserpine, but it differs from reserpine in that it lacks activity at the VMAT1 transporter. The lack of activity at the VMAT1 transporter means that tetrabenazine has less peripheral activity than reserpine and consequently does not produce VMAT1-related side effects such as hypotension.

Tetrabenazine is an effective and safe drug for the treatment of a variety of hyperkinetic movement disorders and, in contrast to typical neuroleptics, has not been demonstrated to cause tardive dyskinesia. Nevertheless, tetrabenazine does exhibit a number of dose-related side effects including causing depression, parkinsonism, drowsiness, nervousness or anxiety, insomnia and, in rare cases, neuroleptic malignant syndrome, see for example the introductory section of WO2016/127133 (Neurocrine Biosciences).

The chemical structure of tetrabenazine is as shown below.

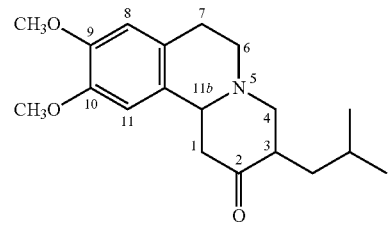

Structure of tetrabenazine

The compound has chiral centres at the 3 and 11 b carbon atoms and hence can, theoretically, exist in a total of four isomeric forms, as shown below.

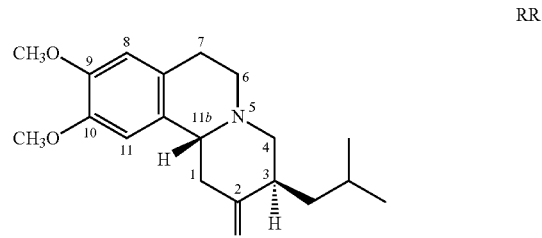

RR

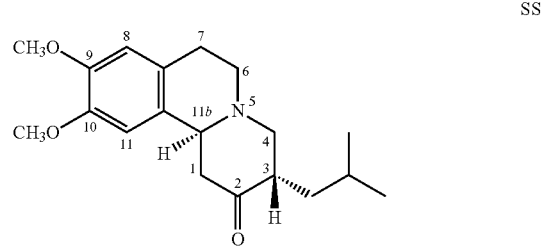

SS

RS

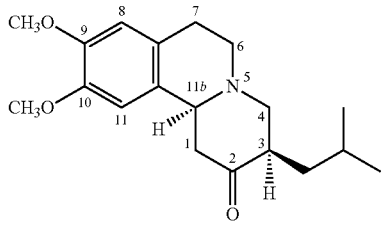

SR

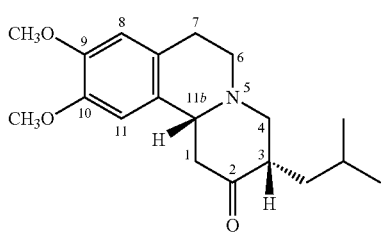

Possible tetrabenazine isomers

The stereochemistry of each isomer is defined using the "R and S" nomenclature developed by Cahn, Ingold and Prelog, see *Advanced Organic Chemistry* by Jerry March, 4th Edition, John Wiley & Sons, New York, 1992, pages 109-114. In this patent application, the designations "R" or "S" are given in the order of the position numbers of the carbon atoms. Thus, for example, RS is a shorthand notation for 3R,11bS. Similarly, when three chiral centres are present, as in the dihydrotetrabenazines described below, the designations "R" or "S" are listed in the order of the carbon atoms 2, 3 and 11b. Thus, the 2R,3S,11bS isomer is referred to in short hand form as RSS and so on.

Commercially available tetrabenazine is a racemic mixture of the RR and SS isomers and it would appear that the RR and SS isomers are the most thermodynamically stable isomers.

Tetrabenazine has somewhat poor and variable bioavailability. It is extensively metabolised by first-pass metabolism, and little or no unchanged tetrabenazine is typically detected in the urine. It is known that at least some of the metabolites of tetrabenazine are dihydrotetrabenazines formed by reduction of the 2-keto group in tetrabenazine.

Dihydrotetrabenazine (Chemical name: 2-hydroxy-3-(2-methylpropyl)-1,3,4,6,7,11b-hexahydro-9,10-dimethoxy-benzo(a)quinolizine) has three chiral centres and can therefore exist in any of the following eight optical isomeric forms:

RRR

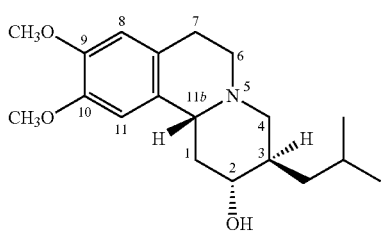

SSS

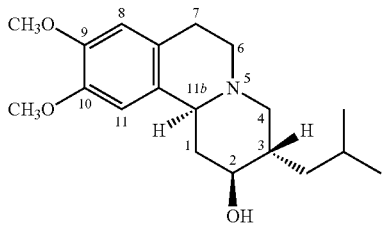

SRR

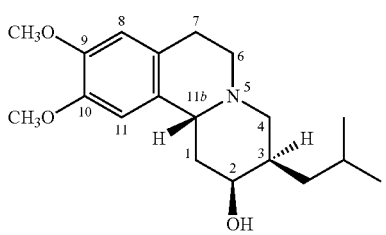

RSS

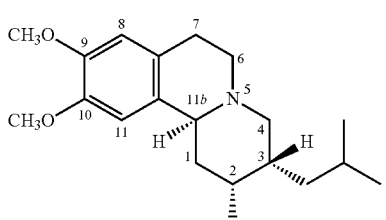

SSR

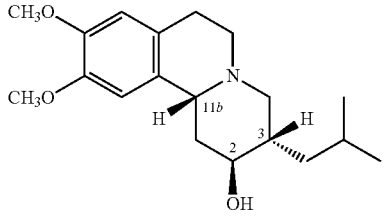

RRS

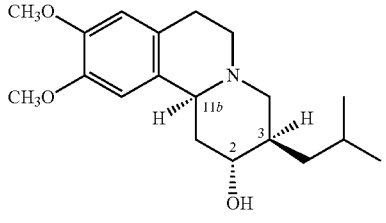

RSR

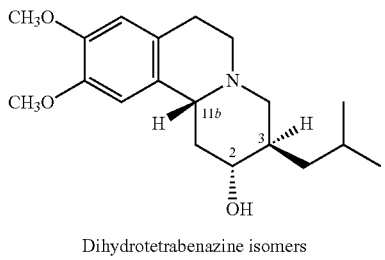

Dihydrotetrabenazine isomers

The synthesis and characterisation of all eight dihydrotetrabenazine isomers is described by Sun et al. (*Eur. J. Med. Chem.* (2011), 1841-1848).

Of the eight dihydrotetrabenazine isomers, four isomers are derived from the RR and SS isomers of the parent tetrabenazine, namely the RRR, SSS, SRR and RSS isomers.

The RRR and SSS isomers are commonly referred to as "alpha (α)" dihydrotetrabenazines and can be referred to individually as (+)-α-dihydrotetrabenazine and (−)-α-dihydrotetrabenazine respectively. The alpha isomers are characterised by a trans relative orientation of the hydroxyl and 2-methylpropyl substituents at the 2- and 3-positions — see for example, Kilbourn et al., Chirality, 9:59-62 (1997) and Brossi et al., Helv. Chim. Acta., vol. XLI, No. 193, pp1793-1806 (1958.

The SRR and RSS isomers are commonly referred to as "beta (β)" isomers and can be referred to individually as (+)-β-dihydrotetrabenazine and (−)-β-dihydrotetrabenazine respectively. The beta isomers are characterised by a cis relative orientation of the hydroxyl and 2-methylpropyl substituents at the 2- and 3-positions.

Although dihydrotetrabenazine is believed to be primarily responsible for the activity of the drug, there have been no studies published to date that contain evidence demonstrating which of the various stereoisomers of dihydrotetrabenazine is responsible for its biological activity. More specifically, there have been no published studies demonstrating which of the stereoisomers is responsible for the ability of tetrabenazine to treat movement disorders such as Tourette's syndrome.

Schwartz et al. (*Biochem. Pharmacol.* (1966), 15: 645-655) describes metabolic studies of tetrabenazine carried out in rabbits, dogs and humans. Schwartz et al. identified nine metabolites, five of which were unconjugated and the other four of which were conjugated with glucuronic acid. The five unconjugated metabolites were the alpha- and beta-dihydrotetrabenazines, their two oxidised analogues in which a hydroxyl group has been introduced into the 2-methylpropyl side chain, and oxidised tetrabenazine in which a hydroxyl group has been introduced into the 2-methylpropyl side chain. The four conjugated metabolites were all compounds in which the 9-methoxy group had been demethylated to give a 9-hydroxy compound. The chirality of the various metabolites was not studied and, in particular, there was no disclosure of the chirality of the individual α- and β-isomers. Scherman et al., (*Mol. Pharmacol.* (1987), 33, 72-77 describes the stereospecificity of VMAT2 binding between racemic α- and β-dihydrotetrabenazine. They reported that α-dihydrotetrabenazine had a 3- to 4-fold higher affinity for the Chromaffin Granule Monoamine Transporter than the β-isomer, when studied in vitro. However, Scherman et al. does not disclose the resolution or testing of the individual enantiomers of the α- and β-dihydrotetrabenazines.

Mehvar et al. (*J. Pharm. Sci.* (1987), 76(6), 461-465) reported a study of the concentrations of tetrabenazine and dihydrotetrabenazine in the brains of rats following administration of either tetrabenazine or dihydrotetrabenazine. The study showed that despite its greater polarity, dihydrotetrabenazine was able to cross the blood-brain barrier. However, the stereochemistry of the dihydrotetrabenazine was not disclosed.

Mehvar et al. (*Drug Metabolism and Disposition* (1987), 15:2, 250-255) describes studies of the pharmacokinetics of tetrabenazine and dihydrotetrabenazine following administration of tetrabenazine to four patients affected by tardive dyskinesia. Oral administration of tetrabenazine resulted in low plasma concentrations of tetrabenazine but relatively high concentrations of dihydrotetrabenazine. However, the stereochemistry of the dihydrotetrabenazine formed in vivo was not reported.

Roberts et al. (*Eur. J. Clin. Pharmacol.* (1986), 29: 703-708) describes the pharmacokinetics of tetrabenazine and its hydroxy-metabolite in patients treated for involuntary movement disorders. Roberts et al. reported that tetrabenazine was extensively metabolised after oral administration resulting in very low plasma concentrations of tetrabenazine but much higher concentrations of a hydroxymetabolite. Although they did not describe the identity of the hydroxymetabolites, they suggested that the high plasma concentrations of the hydroxymetabolites may be therapeutically important (since the metabolites were known to be pharmacologically active) and that, in view of the disclosure in Schwartz et al. (idem), the combination of cis and trans isomers (i.e. alpha and beta isomers) could be more therapeutically important than the parent drug.

Michael Kilbourn and collaborators at the University of Michigan Medical School have published a number of studies relating to the various isomers of dihydrotetrabenazines. In *Med. Chem. Res.* (1994), 5:113-126, Kilbourn et al. describe the use (+/−)-α-[11C]-dihydrotetrabenazine as in vivo imaging agents for VMAT2 binding studies.

In *Eur. J. Pharmacol* (1995) 278, 249-252, Kilbourn et al. reported competition binding studies using [3H]-tetrabenazine to study the in vitro binding affinity of (+)−, (−)−, and (+/−)-α-DHTBZ. The binding assays gave a Ki value of 0.97 nM for (+)-α-dihydrotetrabenazine and 2.2 μM for (−)-α-dihydrotetrabenazine, thereby showing that the (+) alpha isomer has much greater binding affinity for the VMAT2 receptor than the (−) alpha isomer. However, no studies were reported, or conclusions drawn, as to the usefulness of either isomer in the treatment of movement disorders such as Tourette's syndrome.

In Chirality (1997) 9:59-62, Kilbourn et al. described studies aimed at identifying the absolute configuration of (+)-α-dihydrotetrabenazine from which they concluded that it has the 2R, 3R, 11bR configuration shown above. They also referred to the Schwartz et al. and Mehvar et al. articles discussed above as indicating that the α- and β-dihydrotetrabenazines are likely to be the pharmacologically active agents in the human brain but they drew no explicit conclusions as to the precise stereochemical identities of the active metabolites of tetrabenazine.

In *Synapse* (2002), 43:188-194, Kilbourn et al. described the use of (+)-α-[11C]-dihydrotetrabenazine as an agent used to measure specific in vivo binding of the VMAT receptor, in "infusion to equilibrium methods". They found that (−)-α-[11C]-dihydrotetrabenazine produced a uniform brain distribution, consistent with the earlier observations that this enantiomer has a low VMAT affinity.

Sun et al. (idem) investigated the VMAT2 binding affinities of all eight dihydrotetrabenazine isomers. They found that all of the dextrorotatory enantiomers exhibited dramatically more potent VMAT2 binding activity than their corresponding laevorotatory enantiomers with the most active (+)-α-isomer being found to be the most active. However, Sun et al. did not carry out any investigations into the relative efficacies of the individual isomers in treating movement disorders such as Tourette's syndrome.

WO 2011/153157 (Auspex Pharmaceutical, Inc.) describes deuterated forms of dihydrotetrabenazine. Many deuterated forms of dihydrotetrabenazine are depicted but the application only provides sufficient information to allow a small number of the depicted compounds to be synthesised. Although racemic mixtures of $d_6$-α-dihydrotetrabenazine and $d_6$-β-dihydrotetrabenazine as disclosed, these mixtures were not resolved and the properties of the individual (+) and (−) isomers are not studied. Similarly, WO 2014/047167 (Auspex Pharmaceutical, Inc.) describes number of deuterated forms of tetrabenazine and its derivatives. Again, the individual (+) and (−) isomers of deuterated forms of α- and β-dihydrotetrabenazine were not separated or studied.

WO 2006/053067 (Prestwick) described the use of combinations of amantadine and tetrabenazine for treating hyperkinetic movement disorders. Although the document is primarily concerned with using tetrabenazine, it is envisaged that amantadine can be administered with a "tetrabenazine compound" which may be tetrabenazine or dihydrotetrabenazine.

The Examples section of the patent application only discloses experimental protocols of how the combinations of amantadine and tetrabenazine could be administered. Based on the wording of the Examples section, it appears that the combinations had not been administered at the time the application was filed and the application contains no results demonstrating the efficacy of combinations of amantadine and tetrabenazine.

In addition, the Examples section only describes the use of tetrabenazine rather than any dihydrotetrabenazine isomers.

It is evident that, up to the present, it has been unclear as to precisely which dihydrotetrabenazine isomers are responsible for the therapeutic properties resulting from the administration of tetrabenazine. It has previously been assumed that (+)-α-dihydrotetrabenazine is the metabolite of tetrabenazine that is primarily responsible for its therapeutic effects (see WO 2015/171802 Neurocrine Biosciences, Inc.), but this has not been demonstrated experimentally.

As discussed above, the studies carried out by Schwartz et al. (referred to above) demonstrated that both alpha and beta isomers of tetrabenazine are formed as metabolites of tetrabenazine. However, the precise stereochemical configurations of the alpha and beta isomers were not investigated.

Studies in human subjects carried out by the present applicants and described in Example 1 below have confirmed the findings of Schwartz et al. that major metabolites of tetrabenazine are indeed alpha and beta dihydrotetrabenazines.

However, contrary to what has previously been suggested, the main metabolites produced upon administration of tetrabenazine are the (−)-α-dihydrotetrabenazine isomer, which is essentially active as a VMAT2 binding agent, and the (+)-β-dihydrotetrabenazine isomer, which is significantly less active than the (+)-α-dihydrotetrabenazine isomer.

Thus, in a single dose study involving the administration of tetrabenazine to adult male humans, the $C_{max}$ figures for (+)-β-dihydrotetrabenazine and (−)-α-dihydrotetrabenazine respectively were 103 and 72.94 ng/ml whereas the $C_{max}$ figures for (−)β-dihydrotetrabenazine and (+)-α-dihydrotetrabenazine respectively were 5.28 and 2.61 ng/ml. The area under the curve (AUC) figures for each of the (+)-β-dihydrotetrabenazine, (−)-α-dihydrotetrabenazine, (−)-β-dihydrotetrabenazine and (+)-α-dihydrotetrabenazine metabolites respectively were 375.78, 305.84, 16.28 and 7.98. A similar distribution of metabolites was found when multiple doses of tetrabenazine were administered.

The data suggest that (+)-α-dihydrotetrabenazine is not primarily responsible for the therapeutic properties of tetrabenazine. On the contrary, it appears that (+)-α-dihydrotetrabenazine may be responsible for a relatively small contribution to the therapeutic properties of tetrabenazine.

The importance of preparing enantiopure compositions for treatment of the human and animal body is known. It is well known that enantiomers may have different biological properties, for example wherein one enantiomer is useful for the treatment of a specific disease or condition and wherein the other enantiomer is toxic or produces unwanted side effects. An example of this is the drug thalidomide, which was marketed as a sedative and also prescribed to pregnant women to treat morning sickness, but it was later found that one enantiomer caused birth defects in children of the women who had been administered thalidomide during their pregnancy.

Guidance from the FDA regarding enantiomers states that applications for drug substances and drug products should include a stereochemically specific identity test and/or a stereochemically selective assay method.

Even in cases where one of the enantiomers is medically useful and the other is inactive and shows no side effects, it may still be advantageous to remove the inactive enantiomer in order to reduce the size of the dosage form administered to patients.

SUMMARY OF THE INVENTION

It has now surprisingly been found that combinations of (+)- and (−)-α-dihydrotetrabenazine are more effective in the reduction of locomotor activity in amphetamine induced rats than (+)-α-dihydrotetrabenazine alone, despite the fact that it has been previously reported that the (−)-α-dihydrotetrabenazine is a poor VMAT2 inhibitor.

It has also been shown that both racemic and scalemic (i.e. non-racemic) combinations exhibit enhanced efficacy Studies confirmed the inactivity of (−)-α-dihydrotetrabenazine in treating movement disorders when administered alone (see Example 2, Study 1). However, it was unexpectedly found that when (−)-α-dihydrotetrabenazine was administered in combination with (+)-α-dihydrotetrabenazine, an improved effect was seen when compared to the administration of the (+)-isomer alone (see Example 2, Studies 3 and 4). It is thought that this improved effect may be due to the binding of (−)-α-dihydrotetrabenazine to proteins other than VMAT2, which may play a role in mediating hyperkinetic movement disorders.

On the basis of the studies carried out to date, it is envisaged that combinations of (+)- and (−)-α-dihydrotetrabenazine will be useful in the prophylaxis or treatment of the disease states and conditions for which tetrabenazine is currently used or proposed. Thus, by way of example, and without limitation, the dihydrotetrabenazine compounds of the invention may be used for the treatment of movement disorders and in particular hyperkinetic movement disorders such as Huntington's disease, hemiballismus, senile chorea, tic disorders, tardive dyskinesia, dystonia and Tourette's syndrome.

Accordingly, in a first aspect, the invention provides a pharmaceutical unit dosage form comprising (+)-α-dihydrotetrabenazine and (−)-α-dihydrotetrabenazine, or pharmaceutically acceptable salts thereof, and a pharmaceutically acceptable excipient.

In another aspect, the invention provides a combination of (+)-α-dihydrotetrabenazine and (−)-α-dihydrotetrabenazine, or pharmaceutically acceptable salts thereof, for use in medicine. (+)-α-Dihydrotetrabenazine is believed to have the chemical structure (I) shown below:

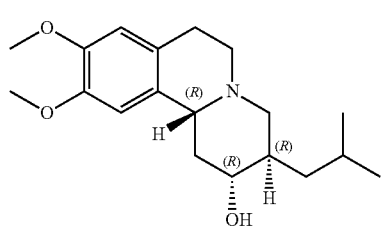

(−)-α-Dihydrotetrabenazine is believed to have the chemical structure (II) shown below:

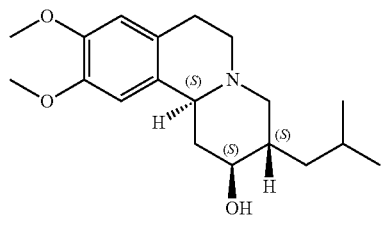

In another aspect, the invention provides a combination of (+)-α-dihydrotetrabenazine and (−)-α-dihydrotetrabenazine, or pharmaceutically acceptable salts thereof, for use in medicine.

In a further aspect, the invention provides a combination of (+)-α-dihydrotetrabenazine and (−)-α-dihydrotetrabenazine, or pharmaceutically acceptable salts thereof (pharmaceutical unit dosage form as hereinbefore defined), for use in the treatment of a movement disorder.

In further embodiments, the invention provides:
A method of treatment of a movement disorder in a subject in need thereof (e.g. a mammalian subject such as a human), which treatment comprises administering to the subject a combination of (+)-α-dihydrotetrabenazine and (−)-α-dihydrotetrabenazine, or pharmaceutically acceptable salts thereof.

The use of a combination of (+)-α-dihydrotetrabenazine and (−)-α-dihydrotetrabenazine, or pharmaceutically acceptable salts thereof, for the manufacture of a medicament for the treatment of a movement disorder.

The inventors have also found that low doses (i.e. of 20 mg or less per day) of (+)-α-dihydrotetrabenazine may be useful in the treatment of movement disorders and it is therefore envisaged that such low doses of (+)-α-dihydrotetrabenazine, in combination with (−)-α-dihydrotetrabenazine, will also be useful in treating movement disorders.

Accordingly, in another embodiment, the invention provides a combination of (+)-α-dihydrotetrabenazine and (−)-α-dihydrotetrabenazine, or pharmaceutically acceptable salts thereof, for use in a method of treatment of a movement disorder, wherein the method comprises administering to a subject (.e.g. a human subject) in need thereof an effective therapeutic amount of the combination sufficient to provide a dosage of from 1 mg to 20 mg of (+)-α-dihydrotetrabenazine per day.

In further aspects, the invention provides:
A method of treatment of movement disorders, wherein the method comprises administering to a subject (.e.g. a human subject) in need thereof an effective therapeutic amount of a combination of (+)-α-dihydrotetrabenazine and (−)-α-dihydrotetrabenazine, or pharmaceutically acceptable salts thereof, sufficient to provide a dosage of from 1 mg to 20 mg of (+)-α-dihydrotetrabenazine per day.

The use of a combination of (+)-α-dihydrotetrabenazine and (−)-α-dihydrotetrabenazine, or pharmaceutically acceptable salts thereof, for the manufacture of a medicament for the treatment of a movement disorder, wherein the method comprises administering to a subject (.e.g. a human subject) in need thereof an effective therapeutic amount of the combination sufficient to provide a dosage of from 1 mg to 20 mg of (+)-α-dihydrotetrabenazine per day.

The use of a (−)-α-dihydrotetrabenazine, or a pharmaceutically acceptable salt thereof, for the manufacture of a medicament for administration in combination with (+)-α-dihydrotetrabenazine or a pharmaceutuically acceptable salt thereof for a method of treatment of a movement disorder, wherein the method comprises administering to a subject (.e.g. a human subject) in need thereof an effective therapeutic amount of the combination sufficient to provide a dosage of from 1 mg to 20 mg of (+)-α-dihydrotetrabenazine per day.

In each of the foregoing embodiments (i.e. a combination for use, a method, or a use) employing a low dose of (+)-α-dihydrotetrabenazine or a pharmaceutically acceptable salt thereof, the daily dose of (+)-α-dihydrotetrabenazine is from 1 mg to 20 mg.

In particular embodiments, there is provided
A combination for use, a method or a use as described herein, wherein the treatment comprises administering to the subject an amount of (+)-α-dihydrotetrabenazine from 1.5 mg to 20 mg (e.g. between 1.5 mg and 20 mg) per day.

A combination for use, a method or a use as described herein, wherein the treatment comprises administering to the subject an amount of (+)-α-dihydrotetrabenazine from 2 mg to 20 mg (e.g. between 2 mg and 20 mg) per day.

A combination for use, a method or a use as described herein, wherein the treatment comprises administering to the subject an amount of (+)-α-dihydrotetrabenazine from 3 mg to 20 mg (e.g. between 3 mg and 20 mg) per day.

A combination for use, a method or a use as described herein, wherein the treatment comprises administering to the subject an amount of (+)-α-dihydrotetrabenazine from 2 mg to 15 mg (e.g. between 2 mg and 15 mg) per day.

A combination for use, a method or a use as described herein, wherein the treatment comprises administering to the subject an amount of (+)-α-dihydrotetrabenazine from 3 mg to 15 mg (e.g. between 3 mg and 15 mg) per day.

A combination for use, a method or a use as described herein, wherein the treatment comprises administering to the subject an amount of (+)-α-dihydrotetrabenazine from 5 mg to 15 mg (e.g. between 5 mg and 15 mg) per day.

The administration of (+)-α-dihydrotetrabenazine and (−)-α-dihydrotetrabenazine typically forms part of a chronic treatment regime. The (+)-α-dihydrotetrabenazine and (−)-α-dihydrotetrabenazine may therefore be administered to a patient for a treatment period of at least a week, more usually at least two weeks, or at least a month, and typically longer than a month. Where a patient is shown to respond well to treatment, the period of treatment can be longer than six months and may extend over a period of years.

The chronic treatment regime may involve the administration of the (+)-α-dihydrotetrabenazine and (−)-α-dihydrotetrabenazine every day, or the treatment regime may include days when no (+)-α-dihydrotetrabenazine or (−)-α-dihydrotetrabenazine is administered.

The dosage administered to the subject may vary during the treatment period. For example, the initial dosage may be increased or decreased depending on the subject's response to the treatment. A subject may, for example, be given an initial low dose to test the subject's tolerance towards the (+)-α-dihydrotetrabenazine and (−)-α-dihydrotetrabenazine, and the dosage thereafter increased as necessary up to the maximum daily intake of 20 mg. Alternatively, an initial daily dosage administered to the patient may be selected so as to give an estimated desired degree of VMAT2 blockage, following which a lower maintenance dose may be given for the remainder of the treatment period, with the option of increasing the dosage should the subject's response to the treatment indicate that an increase is necessary.

It is envisaged that the quantity of (+)-α-dihydrotetrabenazine and (−)-α-dihydrotetrabenazine required to achieve the desired therapeutic effect will be dependent on the weight of the subject to be treated. The quantities of (+)-α-dihydrotetrabenazine and (−)-α-dihydrotetrabenazine administered to the subject can be expressed in a number of mg/kg, where in the kg relates the weight of the subject to be treated. The appropriate dosage amount can therefore be calculated by multiplying the mg/kg amount by the weight of the subject to be treated.

Accordingly, in another aspect, the invention provides a combination of (+)-α-dihydrotetrabenazine and (−)-α-dihydrotetrabenazine or pharmaceutically acceptable salts thereof, for use in a method for the treatment of a movement disorder, wherein the treatment comprises administering to a subject an amount of the combination of from 0.01 mg/kg to 0.3 mg/kg (e.g. between 0.01 mg/kg and 0.3 mg/kg) per day provided that the total amount of (+)-α-dihydrotetrabenazine administered per day is in the range from 1 mg to 20 mg.

In further aspects, the invention provides:
A method of treatment of a movement disorder in a subject in need thereof (e.g. a mammalian subject such as a human), which treatment comprises administering to the subject a combination of (+)-α-dihydrotetrabenazine and (−)-α-dihydrotetrabenazine, or pharmaceutically acceptable salts thereof, in an amount from 0.01 mg/kg to 0.3 mg/kg (e.g. between 0.01 mg/kg and 0.3 mg/kg) per day, provided that the total amount of (+)-α-dihydrotetrabenazine administered per day is in the range from 1 mg to 20 mg.

The use of a combination of (+)-α-dihydrotetrabenazine and (−)-α-dihydrotetrabenazine, or pharmaceutically acceptable salts thereof for the manufacture of a medicament for the treatment of a movement disorder, which treatment comprises administering to the subject the combination in an amount from 0.01 mg/kg to 0.3 mg/kg (e.g. between 0.01 mg/kg and 0.3 mg/kg), provided that the total amount of (+)-α-dihydrotetrabenazine administered per day is in the range from 1 mg to 20 mg.

In each of the foregoing embodiments (i.e. a combination for use, a method, or a use) wherein a combination of (+)-α-dihydrotetrabenazine and (−)-α-dihydrotetrabenazine, or pharmaceutically acceptable salts thereof, is administered in an amount from 0.01 mg/kg to 0.3 mg/kg (e.g. between 0.01 mg/kg and 0.3 mg/kg) per day, the daily dose of (+)-α-dihydrotetrabenazine is from 1 mg to 20 mg.

In particular embodiments, there is provided:
A combination for use, a method or a use as described herein, wherein the treatment comprises administering to the subject an amount of the combination of from 0.02 mg/kg to 0.3 mg/kg (e.g. between 0.02 mg/kg and 0.3 mg/kg) per day, provided that the total amount of (+)-α-dihydrotetrabenazine administered per day is in the range from 1 mg to 20 mg.

A combination for use, a method or a use as described herein, wherein the treatment comprises administering to the subject an amount of the combination of from 0.03 mg/kg to 0.3 mg/kg (e.g. between 0.03 mg/kg and 0.3 mg/kg) per day, provided that the total amount of (+)-α-dihydrotetrabenazine administered per day is in the range from 1 mg to 20 mg.

A combination for use, a method or a use as described herein, wherein the treatment comprises administering to the subject an amount of the combination from 0.04 mg/kg to 0.3 mg/kg (e.g. between 0.04 mg/kg and 0.3 mg/kg) per day, provided that the total amount of (+)-α-dihydrotetrabenazine administered per day is in the range from 1 mg to 20 mg.

A combination for use, a method or a use as described herein, wherein the treatment comprises administering to the subject an amount of the combination from 0.05 mg/kg to 0.3 mg/kg (e.g. between 0.05 mg/kg and 0.3 mg/kg) of (+)-α-dihydrotetrabenazine, provided that the total amount of (+)-α-dihydrotetrabenazine administered per day is in the range from 1 mg to 20 mg.

The combinations of the invention (and dosage forms containing the combinations) are useful in the treatment of movement disorders, and in particular hyperkinetic movement disorders such as Huntington's disease, hemiballismus, senile chorea, tic disorders, tardive dyskinesia, dystonia and Tourette's syndrome.

More particularly, the combinations of the invention (and dosage forms containing the combinations) are for use in the treatment of a hyperkinetic movement disorder selected from tic disorders, tardive dyskinesia and Tourette's syndrome.

In one particular embodiment, the combinations of the invention (and dosage forms containing the combinations) are for use in the treatment of tardive dyskinesia.

In another particular embodiment, the combinations of the invention (and dosage forms containing the combinations) are for use in the treatment of Tourette's syndrome.

The usefulness of the combinations of the invention in the treatment of movement disorders arises in part from the ability of (+)-α-dihydrotetrabenazine to bind to the vesicular monoamine transporter 2 (VMAT2).

Complete blocking of the VMAT2 proteins is considered undesirable as this can lead to unwanted side effects, such as Parkinsonism. The present invention provides plasma levels of (+)-α-dihydrotetrabenazine and (−)-α-dihydrotetrabenazine that are sufficient to give effective treatment of movement disorders but do not block the VMAT2 proteins to an extent that causes Parkinsonism and similar side effects. The levels of VMAT2 blocking can be determined by competitive binding studies using Positron Emission Tomography (PET). By co-administering a radioactive ligand with the compound of interest at various concentrations, the proportion of binding sites occupied can be determined (see for example, Matthews et al., "Positron emission tomography molecular imaging for drug development", *Br. J. Clin. Pharmacol.*, 73:2, 175-186).

Accordingly, in a further aspect, the invention provides a combination of (+)-α-dihydrotetrabenazine and (−)-α-dihydrotetrabenazine, or pharmaceutically acceptable salts thereof, for use in a method for the treatment of a movement disorder, wherein the treatment comprises administering to a subject an amount of the combination sufficient to cause a level of blocking of from 20% to 90% of VMAT2 proteins in the subject.

In further aspects, the invention provides:

A method of treatment of a movement disorder in a subject in need thereof (e.g. a mammalian subject such as a human), which treatment comprises administering to the subject a combination of (+)-α-dihydrotetrabenazine and (−)-α-dihydrotetrabenazine, or pharmaceutically acceptable salts thereof, sufficient to cause a level of blocking of from 20% to 90% of the VMAT2 proteins in the subject.

The use of a combination of (+)-α-dihydrotetrabenazine and (−)-α-dihydrotetrabenazine, or pharmaceutically acceptable salts thereof, for the manufacture of a medicament for the treatment of a movement disorder in a subject (e.g. a mammalian subject such as a human), which treatment comprises administering to the subject an amount of the combination sufficient to cause a level of blocking of from 20% to 90% of VMAT2 proteins in the subject.

The use of (+)-α-dihydrotetrabenazine, or a pharmaceutically acceptable salt thereof, for the manufacture of a medicament for use in combination with (−)-α-dihydrotetrabenazine or a pharmaceutically acceptable salt thereof for the treatment of a movement disorder in a subject (e.g. a mammalian subject such as a human), which treatment comprises administering to the subject an amount of the combination sufficient to cause a level of blocking of from 20% to 90% of VMAT2 proteins in the subject.

In further embodiments, there is provided:

A combination for use, a method or a use as described herein, wherein the treatment comprises administering to the subject an amount of the combination sufficient to cause a level of blocking of from 25% to 85% of the VMAT2 proteins in the subject.

A combination for use, a method or a use as described herein, wherein the treatment comprises administering to the subject an amount of the combination sufficient to cause a level of blocking of from 30% to 80% of the VMAT2 proteins in the subject.

A combination for use, a method or a use as described herein, wherein the treatment comprises administering to the subject an amount of the combination sufficient to cause a level of blocking of from 35% to 75% of the VMAT2 proteins in the subject.

A combination for use, a method or a use as described herein, wherein the treatment comprises administering to the subject an amount of the combination sufficient to cause a level of blocking of from 35% to 70% of the VMAT2 proteins in the subject.

A combination for use, a method or a use as described herein, wherein the treatment comprises administering to the subject an amount of the combination sufficient to cause a level of blocking of from 40% to 75% of the VMAT2 proteins in the subject.

A combination for use, a method or a use as described herein, wherein the treatment comprises administering to the subject in need thereof, wherein the method comprising administering to a subject an amount of the combination sufficient to cause a level of blocking of from 45% to 75% of the VMAT2 proteins in the subject.

A combination for use, a method or a use as described herein, wherein the treatment comprises administering to the subject in need thereof, wherein the method comprising administering to a subject an amount of the combination sufficient to cause a level of blocking of from 35% to 80% of the VMAT2 proteins in the subject.

A combination for use, a method or a use as described herein, wherein the treatment comprises administering to the subject in need thereof, wherein the method comprising administering to a subject an amount of the combination sufficient to cause a level of blocking of from 40% to 80% of the VMAT2 proteins in the subject.

A combination for use, a method or a use as described herein, wherein the treatment comprises administering to the subject an amount of the combination sufficient to cause a level of blocking of from 45% to 80% of the VMAT2 proteins in the subject.

A combination for use, a method or a use as described herein, wherein the treatment comprises administering to the subject an amount of the combination sufficient to cause a level of blocking of from 50% to 80% of the VMAT2 proteins in the subject.

A combination for use, a method or a use as described herein, wherein the treatment comprises administering to the subject an amount of the combination sufficient to cause a level of blocking of from 55% to 80% of the VMAT2 proteins in the subject.

A combination for use, a method or a use as described herein, wherein the treatment comprises administering to the subject an amount of the combination sufficient to cause a level of blocking of VMAT2 proteins in the subject of from 30% to 70% (e.g. between 30% and 70%).

A combination for use, a method or a use as described herein, wherein the treatment comprises administering to the subject in need thereof, wherein the method comprising administering to a subject an amount of the combination sufficient to cause a blocking level of VMAT2 proteins in the subject of from 30% to 65% (e.g. between 30% and 65%).

A combination for use, a method or a use as described herein, wherein the treatment comprises administering to the subject in need thereof, wherein the method comprising administering to a subject an amount of the combination sufficient to cause a blocking level of VMAT2 proteins in the subject of from 30% to 60% (e.g. between 30% and 60%).

A combination for use, a method or a use as described herein, wherein the treatment comprises administering to the subject in need thereof, wherein the method comprising administering to a subject an amount of the combination sufficient to cause a level blocking of VMAT2 proteins in the subject of from 40% to 80% (e.g. between 40% and 80%).

A combination for use, a method or a use as described herein, wherein the treatment comprises administering to the subject in need thereof, wherein the method comprising administering to a subject an amount of the combination sufficient to cause a level of blocking of VMAT2 proteins in the subject of from 40% to 75% (e.g. between 40% and 75%).

A combination for use, a method or a use as described herein, wherein the treatment comprises administering to the subject in need thereof, wherein the method comprising administering to a subject an amount of the combination sufficient to cause a level of blocking of VMAT2 proteins in the subject of from 40% to 70% (e.g. between 40% and 70%).

A combination for use, a method or a use as described herein, wherein the treatment comprises administering to the subject in need thereof, wherein the method comprising administering to a subject an amount of the combination sufficient to cause a level of blocking of VMAT2 proteins in the subject of from 40% to 65% (e.g. between 40% and 65%).

A combination for use, a method or a use as described herein, wherein the treatment comprises administering to the subject in need thereof, wherein the method comprising administering to a subject an amount of the combination sufficient to cause a level of blocking of VMAT2 proteins in the subject of from 40% to 60% (e.g. between 40% and 60%).

In each of the foregoing aspects and embodiments of the invention, the combinations of (+)-α-dihydrotetrabenazine and (−)-α-dihydrotetrabenazine may be racemic.

Alternatively, in each of the foregoing aspects and embodiments of the invention, the combinations of (+)-α-dihydrotetrabenazine and (−)-α-dihydrotetrabenazine may be scalemic (i.e. non-racemic).

In each of the combinations of the invention, the uses thereof and pharmaceutical dosage forms containing the combinations, as defined above, the ratio of (+)-α-dihydrotetrabenazine to (−)-α-dihydrotetrabenazine in the combination can be, for example, from 0.5:1 to 20:1. In particular embodiments, the ratio of (+)-α-dihydrotetrabenazine to (−)-α-dihydrotetrabenazine in the combination can be a ratio in a range selected from:

(i) 1:1 to 20:1
(ii) 1:1 to 15:1
(iii) 1:1 to 12:1
(iv) 1:1 to 10:1
(v) 1:1 to 5:1
(vi) 1:1 to 4:1
(vii) 1:1 to 3:1
(viii) 1:1 to 2:1
(ix) 1.1:1 to 20:1
(x) 1.1:1 to 15:1
(xi) 1.1:1 to 12:1
(xii) 1.1:1 to 10:1
(xiii) 1.1:1 to 5:1
(xiv) 1.1:1 to 4:1
(xv) 1.1:1 to 3:1
(xvi) 1.1:1 to 2:1
(xvii) 1.2:1 to 20:1
(xviii) 1.2:1 to 15:1
(xix) 1.2:1 to 12:1
(xx) 1.2:1 to 10:1
(xxi) 1.2:1 to 5:1
(xxii) 1.2:1 to 4:1
(xxiii) 1.2:1 to 3:1
(xxiv) 1.2:1 to 2:1

In each of the foregoing aspects and embodiments of the invention, the combinations of (+)-α-dihydrotetrabenazine and (−)-α-dihydrotetrabenazine are typically unaccompanied by other dihydrotetrabenazine isomers.

In some embodiments, minor amounts of other tetrabenazine isomers may be present but these generally are present in amounts corresponding to no more than 20% by weight (i.e. 0.2:1), compared to the total weight of the combination. More usually, other dihydrotetrabenazine isomers are present in amounts corresponding to no more than 10% or 5%, or 2%, or 1% by weight (i.e. 0.2:1), compared to the total weight of the combination.

In each of the foregoing aspects and embodiments of the invention relating to combinations of (+)-α-dihydrotetrabenazine or (−)-α-dihydrotetrabenazine or pharmaceutically acceptable salts thereof, typically, the (+)-α-dihydrotetrabenazine or (−)-α-dihydrotetrabenazine or pharmaceutically acceptable salt thereof, are not administered with a therapeutically effective amount of amantadine. More particularly, the (+)-α-dihydrotetrabenazine or (−)-α-dihydrotetrabenazine, or pharmaceutically acceptable salt thereof, are not administered with any amount of amantadine.

For example, with reference to pharmaceutical unit dosage forms, typically the unit dosage form does not comprise a therapeutically effective amount of amantadine and, more particularly, the pharmaceutical unit dosage form does not comprise any amount of amantadine.

Furthermore, in each of the foregoing aspects and embodiments of the invention relating to (+)-α-dihydrotetrabenazine or (−)-α-dihydrotetrabenazine or pharmaceutically acceptable salts thereof, the pharmaceutical unit dosage form may be other than an extended release or delayed release dosage form.

Thus, for example, the (+)-α-dihydrotetrabenazine or (−)-α-dihydrotetrabenazine, or pharmaceutically acceptable salt thereof, may be administered as an immediate release unit dosage form.

In each of the foregoing aspects and embodiments, the (+)-α-dihydrotetrabenazine and/or (−)-α-dihydrotetrabenazine can be administered as the free base or as a pharmaceutically acceptable salt. In one embodiment, one or both of the (+)-α-dihydrotetrabenazine and (−)-α-dihydrotetrabenazine are administered as pharmaceutically acceptable salts. In another embodiment, both the (+)-α-dihydrotetrabenazine and (−)-α-dihydrotetrabenazine are administered as free bases. Unless stated otherwise, or unless the context indicates otherwise, the quantities of (+)-α-dihydrotetrabenazine and (−)-α-dihydrotetrabenazine are calculated as the amounts of the free base, or when the (+)-α-dihydrotetrabenazine or (−)-α-dihydrotetrabenazine is in the form of a pharmaceutically acceptable salt, the amount of (+)-α-dihydrotetrabenazine or (−)-α-dihydrotetrabenazine per se present in the pharmaceutically acceptable salt.

All references herein to (+)-α-dihydrotetrabenazine include (+)-α-dihydrotetrabenazine both the free base and salts thereof, unless the context indicates otherwise. Likewise all references herein to (−)-α-dihydrotetrabenazine include (−)-α-dihydrotetrabenazine both the free base and salts thereof, unless the context indicates otherwise The salts are typically acid addition salts.

The salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the acid in water or in an organic solvent, or in a mixture of the two; generally, nonaqueous media such as ether, acetone, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

The (+)-α-dihydrotetrabenazine and/or (−)-α-dihydrotetrabenazine may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively 11C, $^{12}C$, $_{13}C$ and $^{14}C$ and $^{16}O$ and $^{18}O$.

Typically, the (+)-α-dihydrotetrabenazine and (−)-α-dihydrotetrabenazine of the invention does not contain isotopes (such as $^{11}C$ or $^3H$) in amounts higher than their natural abundance.

In one embodiment, the percentage of the total hydrogen atoms in the (+)-α-dihydrotetrabenazine and (−)-α-dihydrotetrabenazine that are deuterium atoms is less than 2%, more typically less than 1%, more usually less than 0.1%, preferably less than 0.05% and most preferably no more than 0.02%.

In an analogous manner, a reference to a particular functional group also includes within its scope isotopic variations, unless the context indicates otherwise.

The isotopes may be radioactive or non-radioactive. In one embodiment of the invention, the (+)-α-dihydrotetrabenazine and (−)-α-dihydrotetrabenazine contains no radioactive isotopes. Such compounds are preferred for therapeutic use. In another embodiment, however, the (+)-α-dihydrotetrabenazine and/or (−)-α-dihydrotetrabenazine may contain one or more radioisotopes. Compounds containing such radioisotopes may be useful in a diagnostic context.

References to (+)-α-dihydrotetrabenazine and and (−)-α-dihydrotetrabenazine include any solvates formed by the compounds.

Examples of solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates.

Particular examples of solvates are hydrates such as hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment, either or both of the (+)-α-dihydrotetrabenazine and (−)-α-dihydrotetrabenazine are in an anhydrous form.

Methods for the Preparation of (+)-α-dihydrotetrabenazine and (−)-α-dihydrotetrabenazine)

(+)-α-Dihydrotetrabenazine and (−)-α-dihydrotetrabenazine can be prepared from tetrabenazine according to the synthetic route shown in Scheme 1.

Scheme 1

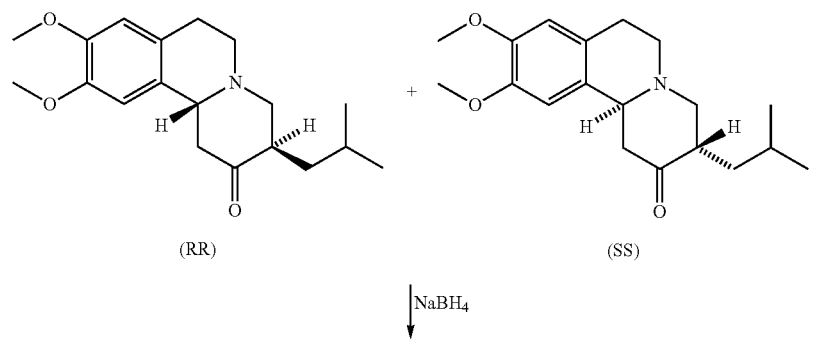

(RR) + (SS)

NaBH$_4$

-continued

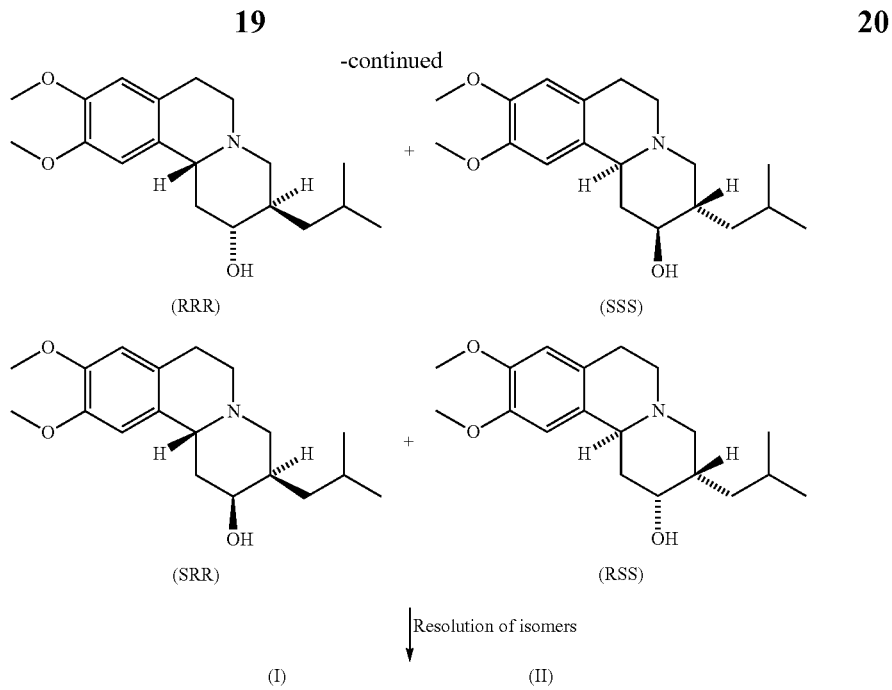

(RRR) + (SSS)

(SRR) + (RSS)

(I) Resolution of isomers (II)

Racemic tetrabenazine (3-isobutyl-9,10-dimethyoxy-1,3,4,6,7,11b-hexahydro-2H-pyrido[2,1,a]isoquinolin-2-one) containing the RR and SS isomers of tetrabenazine is reduced with sodium borohydride to afford a mixture of four dihydrotetrabenazine isomers of which a racemic mixture of the α-dihydrotetrabenazine (RRR and SSS isomers) constitutes the major product and a racemic mixture of the β-dihydrotetrabenazines (the SRR and RSS isomers) constitutes a minor product. The β-dihydrotetrabenazines can be removed during an initial purification procedure, for example by chromatography or recrystallization and then the racemic α-dihydrotetrabenazines resolved by well known methods such as chiral chromatography or the formation of diastereoisomeric salts by reaction with chiral acids followed by separation by recrystallisation.

For example, by recrystallisation of the racemic mixture with di-p-toluoyl-L-tartaric acid or (R)-(−)-camphorsulfonic acid or by chiral chromatography, the (+)-α-dihydrotetrabenazine isomer (I) ((2R, 3R, 11bR)-3-isobutyl-9,10-dimethoxy-1,3,4,6,7,11b-hexahydro-2H-pyrido[2,1,a]isoquinolin-2-ol) can be obtained.

By recrystallisation of the racemic mixture with di-p-toluoyl-R-tartaric acid or (L)-(+)-camphorsulfonic acid or by chiral chromatography, the (−)-α-dihydrotetrabenazine isomer (I) ((2S, 3S, 11bS)-3-isobutyl-9,10-dimethoxy-1,3,4,6,7,11b-hexahydro-2H-pyrido[2,1,a]isoquinolin-2-ol) can be obtained.

(+)-α-Dihydrotetrabenazine and (−)-α-dihydrotetrabenazine can also be prepared according to Yao et al., "Preparation and evaluation of tetrabenazine enantiomers and all eight stereoisomers of dihydrotetrabenazine as VMAT2 inhibitors", Eur. J. Med. Chem., (2011), 46, pp. 1841-1848.

Pharmaceutical Formulations and Methods of Treatment

The pharmaceutical unit dosage forms of the invention can be in any form suitable for oral, parenteral, topical, intranasal, intrabronchial, ophthalmic, otic, rectal, intravaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical unit dosage forms suitable for oral administration include tablets, capsules, caplets, pills, lozenges, syrups, solutions, sprays, powders, granules, elixirs and suspensions, sublingual tablets, sprays, wafers or patches and buccal patches.

Particular examples of pharmaceutical unit dosage forms containing the combinations of the invention are capsules and tablets.

Pharmaceutical unit dosage forms containing the combinations of the invention can be formulated in accordance with known techniques, see for example, Remington's Pharmaceutical Sciences, Mack Publishing Company, Easton, Pa., USA.

Thus, tablet compositions can contain a unit dosage of the combination of active compounds together with an inert diluent or carrier such as a sugar or sugar alcohol, e.g.; lactose, sucrose, sorbitol or mannitol; and/or a non-sugar derived diluent such as sodium carbonate, calcium phosphate, talc, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.: tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the (+)-α-dihydrotetrabenazine and (−)-α-dihydrotetrabenazine, or pharmaceutically acceptable salts thereof making up the combinations of the invention can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped mouldable or waxy material containing the active compound.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the combination of (+)-α-dihydrotetrabenazine and (−)-α-dihydrotetrabenazine, or pharmaceutically acceptable salts thereof together with an inert solid powdered diluent such as lactose.

The (+)-α-dihydrotetrabenazine and (−)-α-dihydrotetrabenazine, and their respective salts can be formulated separately and used in combination, or they can be formulated together. When formulated together, they can be provided as a mixture to which one or more pharmaceutical excipients is (are) added before processing (e.g. compressing to form a tablet or filling into a capsule) to form a pharmaceutical composition such as a unit dosage form. Alternatively, at least some of the (+)-α-dihydrotetrabenazine and (−)-α-dihydrotetrabenazine can be formulated separately in different granules, pellets, microbeads or mini-tablets and then brought together and processed to give a pharmaceutical composition (e.g. by filling into a capsule or compressing to form a tablet). As another alternative, the (+)-α-dihydrotetrabenazine and (−)-α-dihydrotetrabenazine can be contained within different layers in a multi-layered tablet. In another alternative, the (+)-α-dihydrotetrabenazine and (−)-α-dihydrotetrabenazine can each be added separately to an excipient or mixture of excipients and then formulated together.

Particular pharmaceutical compositions of the invention are compositions selected from:

Sublingual compositions;

Intranasal;

Pellets or tablets formulated to provide release kinetics corresponding to zero order release of the active compound;

Pellets or tablets formulated to provide first fast release followed by constant rate release (zero order) of the active compound;

Pellets or tablets formulated to provide a mixture of first order and zero order release of the active compound; and Pellets or tablets formulated to provide a combination of zero order and first order release of the active compound; and optionally a further order of release of the active compound selected from second, third and fourth orders of release and combinations thereof.

Pellets and tablets formulated to provide release kinetics of the types defined above can be prepared according to methods well known the skilled person; for example as described in Remington's Pharmaceutical Sciences (idem) and "Remington — The Science and Practice of Pharmacy, 21st edition, 2006, ISBN 0-7817-4673-6.

The combinations of the invention will generally be presented in pharmaceutical unit dosage form and, as such, will typically contain sufficient compound to provide a desired level of biological activity, as described above.

The combinations of the invention will be administered to a subject (patient) in need thereof (for example a human or animal patient) in an amount sufficient to achieve the desired therapeutic effect, as described above.

EXAMPLES

Figure 1:
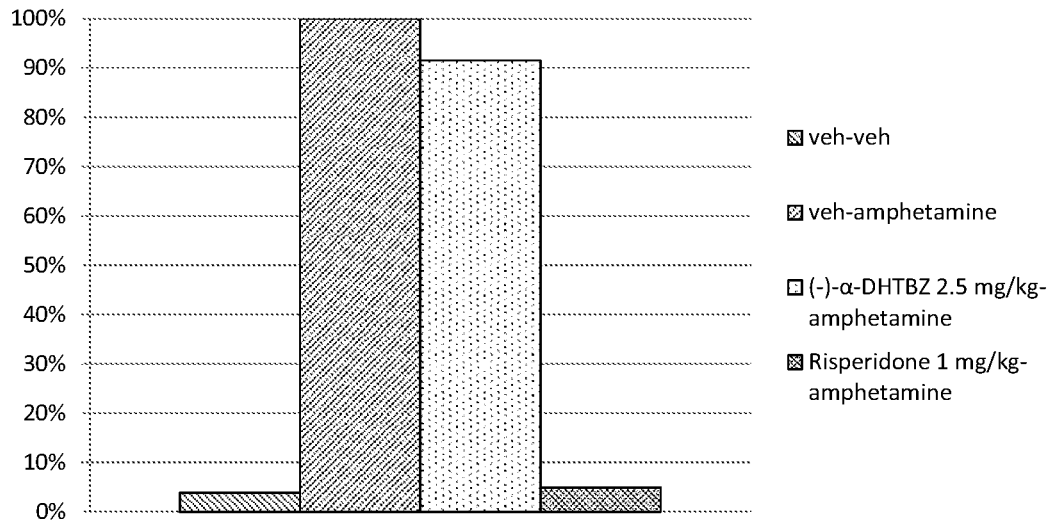
FIG. 1 shows the average total distance travelled by rats when treated with vehicle (with or without amphetamine induction) and (−)-α-dihydrotetrabenazine at a dose of 2.5 mg/kg and risperidone at a dose of 1 mg/kg in amphetamine-induced rats, as described in Example 2, Study 1 below.

The following non-limiting examples illustrate the synthesis and properties of the compositions of the invention.

Example 1

An Investigation into the Nature of the Dihydrotetrabenazine Metabolites Formed After Administration of Tetrabenazine o Human Subjects A pharmacokinetic study was carried out in healthy adult male volunteers under fasting conditions at a dose of single and multiple oral administration of 25 mg tablets once a day to ascertain the plasma levels of +/−α and +/−αdihydrotetrabenazine. The data are summarised below.

Table 1 summarises the pharmacokinetic data obtained following single-dose oral administration of tetrabenazine at a dose level of 25 mg (fasting, N=08).

The data presented in Tables 1 and 2 demonstrate that, in humans, the major metabolites are the (−)-α-dihydrotetrabenazine isomer, which is essentially active as a VMAT2 binding agent, and the (+)-β-dihydrotetrabenazine isomer, which is significantly less active than the (+)-α-dihydrotetrabenazine isomer. (−)13-Dihydrotetrabenazine and (+)-α-dihydrotetrabenazine were shown to be minor metabolites The data suggest that (+)-α-dihydrotetrabenazine is not primarily responsible for the therapeutic properties of tetrabenazine. On the contrary, it appears that (+)-α-dihydrotetrabenazine may be responsible for a relatively small contribution to the therapeutic properties of tetrabenazine.

Example 2

Investigation of the Effect of Combinations of (+)-α-Dihydrotetrabenazine and (−)-α-Dihydrotetrabenazine on Locomotor Activity and Stereotypies in Rats The effects of combinations of (+)-α-dihydrotetrabenazine and (−)-α-dihydrotetrabenazine on locomotor activity and stereotypies in rats were investigated and compared to the effects of the individual (+)-α-dihydrotetrabenazine and (−)-α-dihydrotetrabenazine isomers.

Materials and Methods

Equipment

Open field arena, Med Associates Inc.

Plastic syringes 1 ml, Terumo. Ref: SS-01T1

Animal feeding needle 15 G, Instech Solomon, Cat: 72-4446

Sartorius Mechatronics Scale A22101, Sartorius Weighting Technology, Germany

Needle 27 G Terumo Myjector, 0,5 ml, Ref: 8300010463

Plastic syringes 3 ml, Soft-Ject, Ref: 8300005761

BD Microtainer K2EDTA tubes Ref: 365975

Matrix 0,75 ml, Alphanum Tubes, Thermo Scientific, Ref: 4274

Microplate Devices, Uniplate 24 wells, 10 ml, Ref: 734-1217

TABLE 1

| Analyte | $T_{max}$ Mean (h) | $C_{max}$ (ng/mL) | AUC(0-t) (ng · h/mL) | AUC(0-inf.) (ng · h/mL) | $K_{el}$ NA | Half-life (Mean) (h) | Extrapolated AUC (%) |
|---|---|---|---|---|---|---|---|
| Tetrabenazine | 0.87 | 0.58 | 1.87 | 2.42 | 0.19 | 4.35 | 27.54 |
| (+) α-DHTBZ | 1.16 | 2.61 | 7.98 | 10.83 | 0.17 | 4.79 | 32.10 |
| (−) α-DHTBZ | 0.938 | 72.94 | 305.84 | 351.80 | 0.10 | 7.89 | 10.59 |
| (+) β-DHTBZ | 1.125 | 103.00 | 375.78 | 410.46 | 0.13 | 5.80 | 5.03 |
| (−) β-DHTBZ | 1.03 | 5.28 | 16.28 | 18.77 | 0.45 | 12.98 | 17.66 |

Table 2 summarises the pharmacokinetic data obtained following multiple-dose oral administration of tetrabenazine at a dose level of 25 mg (fasting, N=07).

TABLE 2

| Analyte | $T_{maxss}$ Mean (h) | $C_{maxss}$ (ng/mL) | $C_{minss}$ (ng/mL) | AUC(0-t) (ng · h/mL) | $C_{tss}$ (ng/mL) | $C_{avg}$ (ng · h/mL) |
|---|---|---|---|---|---|---|
| Tetrabenazine | 96.89 | 0.73 | 0.01 | 2.79 | 0.10 | 0.12 |
| (+) α-DHTBZ | 97.18 | 3.31 | 0.00 | 13.74 | 0.44 | 0.57 |
| (−) α-DHTBZ | 96.96 | 98.34 | 5.61 | 474.17 | 6.10 | 19.76 |
| (+) β-DHTBZ | 97.11 | 144.76 | 5.45 | 598.76 | 5.54 | 24.95 |
| (−) β-DHTBZ | 97.11 | 7.78 | 0.16 | 25.17 | 0.57 | 1.05 |

Thermo Electron Corp. Heraeus Fresco 17, refrigerated centrifuge

Test Animals

All animal experiments were carried out according to the National Institute of Health (NIH) guidelines for the care and use of laboratory animals, and approved by the National Animal Experiment Board, Finland. Male CD (Charles River Laboratories, Germany) at weight range of 200-250 g (165-200 g upon arrival) were used for the experiments. Animals were housed at a standard temperature (22±1° C.) and in a light-controlled environment (lights on from 7 am to 8 pm) with ad libitum access to food and water.

Methods

Locomotor activity of the rats was tested in open field arena. The open field test was performed during the rat light cycle and under a normal lighting evenly distributed to the test chambers. The paths of the rats were recorded by activity monitor (Med. Associates Inc.).

Dosing the vehicle, amphetamine, (+)-α-DHTBZ, (−)-α-DHTBZ or risperidone was done prior to LMA test. The rats were placed in the center of the arena, and the path was recorded for 30 minutes. After 30 minutes of testing vehicle or amphetamine was dosed and the rat was placed in the center of the arena, and the path was recorded for 60 minutes, the total testing time being 90 minutes.

Endpoint, Blood Samples and Tissue Processing

Within 10 minutes from the end of the test animals were euthanized by an overdose of $CO_2$. The terminal blood sample was collected with cardiac puncture from all compound treated rats from each group excluding vehicle rats. 0.5 ml of blood was collected with syringe attached to 18 G needle and moved into precooled K2-EDTA microtubes. The EDTA microtube was inverted several times to mix up the EDTA and blood. Tubes were then immediately put on wet ice and centrifuged (Heraeus Fresco 17) within 10-15 minutes of collecting (9.6×1000 G/10×1000 RPM, +4° C. for 2 min), and 200 μl of plasma was collected in 96-tube plates (Matrix Technologies ScreenMates 0.75 ml Alphanumeric Round-Bottom Storage tubes, PP) on dry ice according to sample map.

After collection of blood the neck was dislocated at the base of the skull. Brain was collected and weighed. Brain weights were recorded and the brain was frozen on dry ice on the 24 well plate.

The plasma and brain samples were stored at −80° C. on dry ice until sent for analysis.

Study 1

Animals were grouped as follows:
Group 1: 10 rats treated with Vehicle (t=0 min) and Vehicle (t=30 min)
Group 2: 10 rats treated with Vehicle (t=0 min) and Amphetamine (t=30 min)
Group 3: 10 rats treated with (−)-α-DHTBZ 2.5 mg/kg (t=0 min) and Amphetamine (t=30 min)
Group 4: 10 rats treated with risperidone 1 mg/kg (t=0 min) and Amphetamine (t=30 min)

Results

1. Distance Travelled

Rats dosed with either vehicle, (−)-α-DHTBZ 2.5 mg/kg or risperidone 1 mg/kg were subjected to LMA testing first for 30 min and then for 60 minutes after vehicle or amphetamine challenge. Resulting locomotor activity was evaluated in 3 min bins and as a total over the testing period. The normalised total distance travelled over the testing time is presented in FIG. 1.

When compared to the vehicle-vehicle group the vehicle-amphetamine and (−)-α-DHTBZ 2.5 mg/kg were significantly different. When compared to vehicle-amphetamine group the vehicle-vehicle and risperidone 1 mg/kg were significantly different.

2. Stereotypic Behaviour

Figure 2:
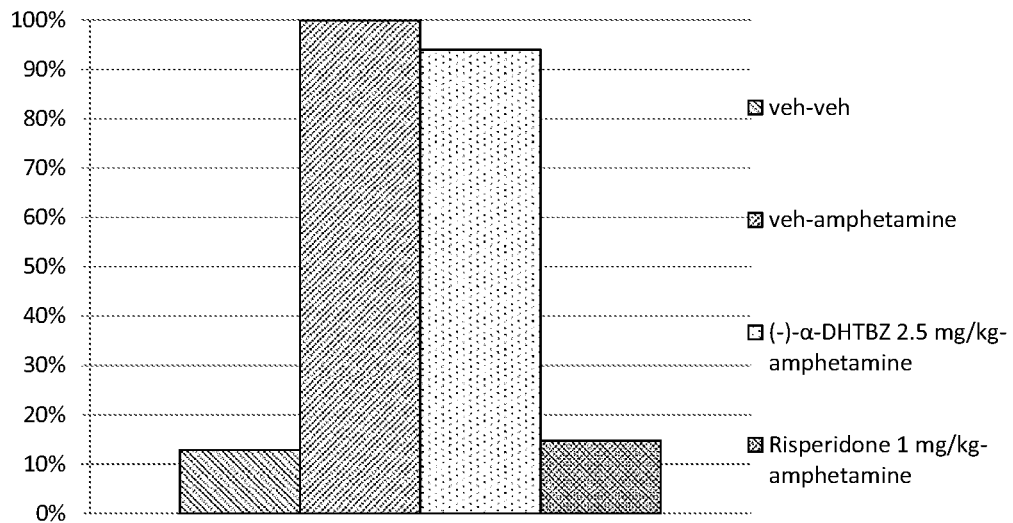
FIG. 2 shows the average total stereotypic behaviour by rats when treated with vehicle (with or without amphetamine induction) and (−)-α-dihydrotetrabenazine at a dose of 2.5 mg/kg and risperidone at a dose of 1 mg/kg in amphetamine-induced rats, as described in Example 2, Study 1 below.

Rats dosed with either vehicle, (−)-α-DHTBZ 2.5 mg/kg or risperidone 1 mg/kg were subjected to LMA testing first for 30 min and then for 60 minutes after vehicle or amphetamine challenge. Resulting stereotypic activity was evaluated in 3 min bins and as a total over the testing period. The normalised total stereotypic behaviour over the testing time is presented in FIG. 2.

When compared to the vehicle-vehicle group the vehicle-amphetamine and (−)-α-DHTBZ 2.5 mg/kg were significantly different. When compared to vehicle-amphetamine group the vehicle-vehicle and risperidone 1 mg/kg were significantly different.

Conclusions

This study evaluated the effect of (−)-α-DHTBZ at dose 2.5 mg/kg and risperidone at dose 1 mg/kg on amphetamine induced locomotor activity in male CD rats.

(−)-α-DHTBZ at dose 2.5 mg/kg did not lead to lower locomotor activity or reduced stereotypic behaviour when compared to the vehicle-amphetamine group. The rats dosed with (−)-α-DHTBZ at dose 2.5 mg/kg were less focused on what was going on around. The rats dosed with (−)-α-DHTBZ were equally active when compared to the vehicle-amphetamine dosed animals suggesting that (−)-α-DHTBZ does not have a sedative effect similar to risperidone.

STUDY 2

The effects on stereotypic behaviour and the distance travelled in rats following administration of (+)-α-dihydrotetrabenazine dosed at 0.1 mg/kg to 0.25 mg/kg, as well as risperidone at 1 mg/kg, were studied.

Animals were grouped as follows:
Group 1: 10 rats treated with Vehicle (t=0 min) and Vehicle (t=30 min)
Group 2: 10 rats treated with Vehicle (t=0 min) and Amphetamine (t=30 min)
Group 3: 10 rats treated with (+)-α-DHTBZ 0.1 mg/kg (t=0 min) and Amphetamine (t=30 min)
Group 4: 10 rats treated with (+)-α-DHTBZ 0.25 mg/kg (t=0 min) and Amphetamine (t=30 min)
Group 5: 10 rats treated with risperidone 1 mg/kg (t=0 min) and Amphetamine (t=30 min)

Results

1 Distance Travelled

Figure 3:
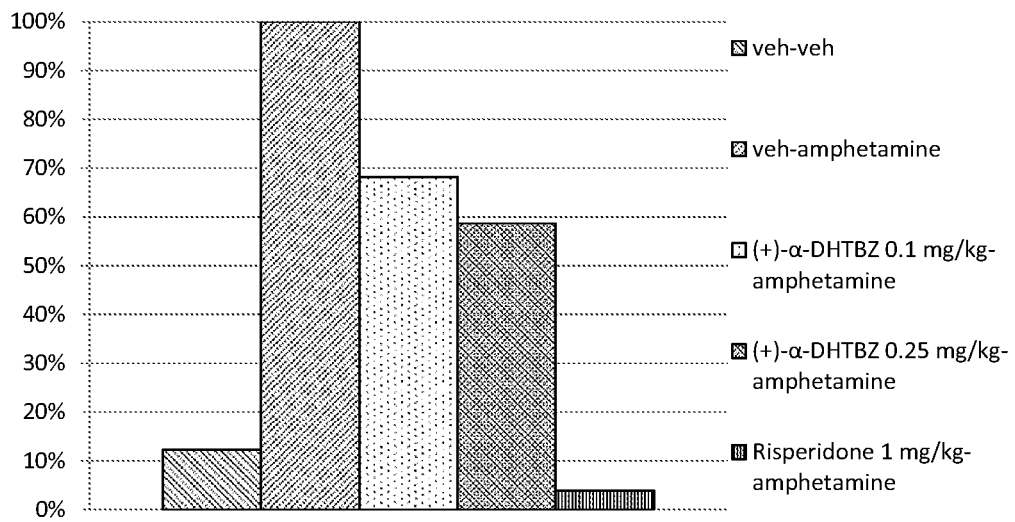
FIG. 3 shows the average total distance travelled by rats when treated with vehicle (with or without amphetamine induction) and (+)-α-dihydrotetrabenazine at doses of 0.1 mg/kg and 0.25 mg/kg and risperidone at a dose of 1 mg/kg in amphetamine-induced rats, as described in Example 2, Study 2 below.

Rats dosed with either vehicle, (+)-α-DHTBZ 0.1 mg/kg, (+)-α-DHTBZ 0.25 mg/kg, or Risperidone 1 mg/kg were subjected to LMA testing first for 30 min and then for 60 minutes after vehicle or amphetamine challenge. Resulting locomotor activity was evaluated in 3 min bins and as a total over the testing period. The normalised total distance travelled over the testing time is presented in FIG. 3.

When compared to vehicle-amphetamine group the vehicle-vehicle, (+)-α-DHTBZ 0.25 mg/kg and risperidone 1 mg/kg were significantly different.

Stereotypic Behaviour

Figure 4:
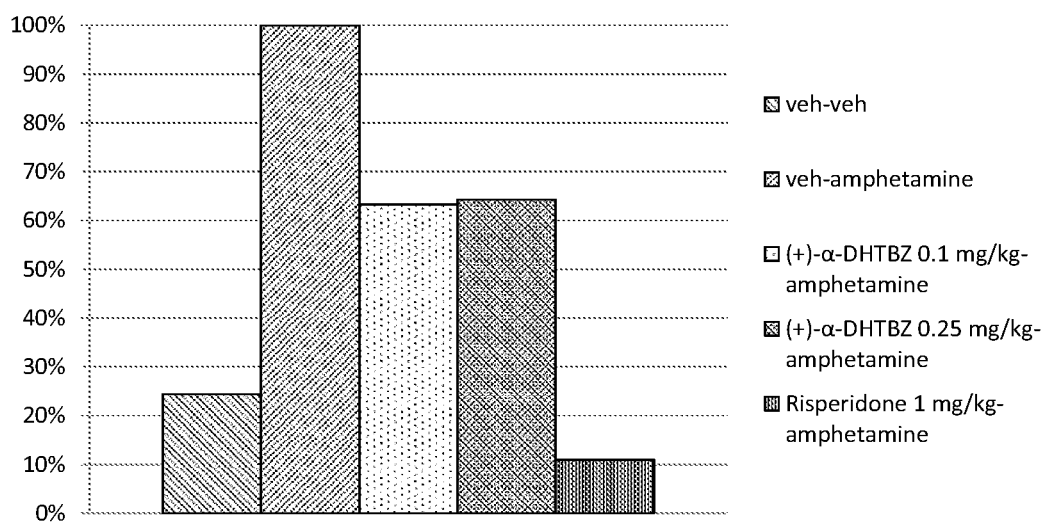
FIG. 4 shows the average total stereotypic behaviour by rats when treated with vehicle (with or without amphetamine induction) and (+)-α-dihydrotetrabenazine at doses of 0.1 mg/kg and 0.25 mg/kg and risperidone at a dose of 1 mg/kg in amphetamine-induced rats, as described in Example 2, Study 2 below.

Rats dosed with either vehicle, (+)-α-DHTBZ 0.1 mg/kg, (+)-α-DHTBZ 0.25 mg/kg, or Risperidone 1 mg/kg were subjected to LMA testing first for 30 min and then for 60 minutes after vehicle or amphetamine challenge. Resulting stereotypic activity was evaluated in 3 min bins and as a total over the testing period. The normalised total stereotypic behaviour over the testing time is presented in FIG. 4.

When compared to vehicle-amphetamine group the vehicle-vehicle, (+)-α-DHTBZ 0.1 mg/kg, (+)-α-DHTBZ 0.25 mg/kg and risperidone 1 mg/kg were significantly different.

Conclusions

This study evaluated the effect of (+)-α-DHTBZ at doses 0.1 mg/kg and 0.25 mg/kg and risperidone at dose 1 mg/kg on amphetamine induced locomotor activity in male CD rats.

(+)-α-DHTBZ at 0.25 mg/kg and risperidone 1 mg/kg led to lower locomotor activity when compared to the vehicle-amphetamine group. (+)-α-DHTBZ at both the tested doses and risperidone 1 mg/kg led to reduced stereotypic behaviour when compared to the vehicle-amphetamine group.

STUDY 3

Animals were grouped as follows:
Group 1: 10 rats treated with Vehicle (t=0 min) and Vehicle (t=30 min)
Group 2: 10 rats treated with Vehicle (t=0 min) and Amphetamine (t=30 min)
Group 3: 10 rats treated with (+)-α-DHTBZ 2 mg/kg (t=0 min) and Amphetamine (t=30 min)
Group 4: 10 rats treated with (+)-α-DHTBZ 2 mg/kg with (−)-α-DHTBZ 2 mg/kg (t=0 min) and Amphetamine (t=30 min)
Group 5: 10 rats treated with risperidone 1 mg/kg (t=0 min) and Amphetamine (t=30 min)

Results

1 Distance Travelled

Figure 5:
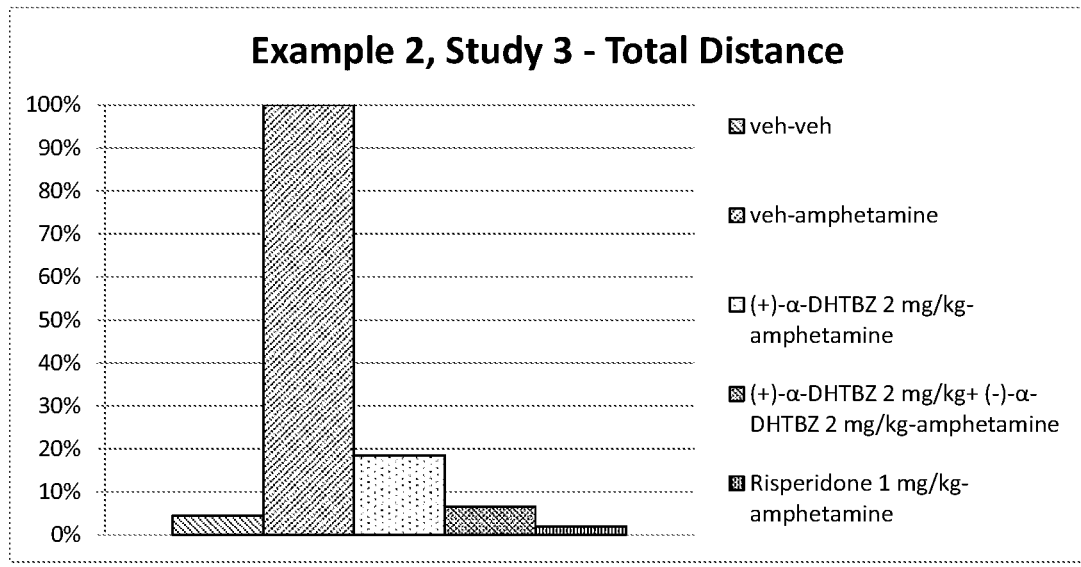
FIG. 5 shows the average total distance travelled by rats when treated with vehicle (with or without amphetamine induction) and (−)-α-dihydrotetrabenazine at a dose of 2 mg/kg, a combination of (+)-α-dihydrotetrabenazine at a dose of 2 mg/kg and (−)-α-dihydrotetrabenazine at a dose of 2 mg/kg, and risperidone at a dose of 1 mg/kg in amphetamine-induced rats, as described in Example 2, Study 3 below.

Rats dosed with either vehicle, (+)-α-DHTBZ 2 mg/kg, the combination of (−)-α-DHTBZ 2 mg/kg and (+)-α-DHTBZ 2 mg/kg or Risperidone 1 mg/kg were subjected to LMA testing first for 30 min and then for 60 minutes after vehicle or amphetamine challenge. Resulting locomotor activity was evaluated in 3 min bins and as a total over the testing period. The normalised total distance travelled over the testing time is presented in FIG. 5.

When compared to the vehicle-vehicle group the vehicle-amphetamine was significantly different. When compared to vehicle-amphetamine group the vehicle-vehicle, (+)-α-DHTBZ 2 mg/kg, the combination of (−)-α-DHTBZ 2 mg/kg and (+)-α-DHTBZ 2 mg/kg and risperidone 1 mg/kg were significantly different.

2 Stereotypic Behaviour

Figure 6:
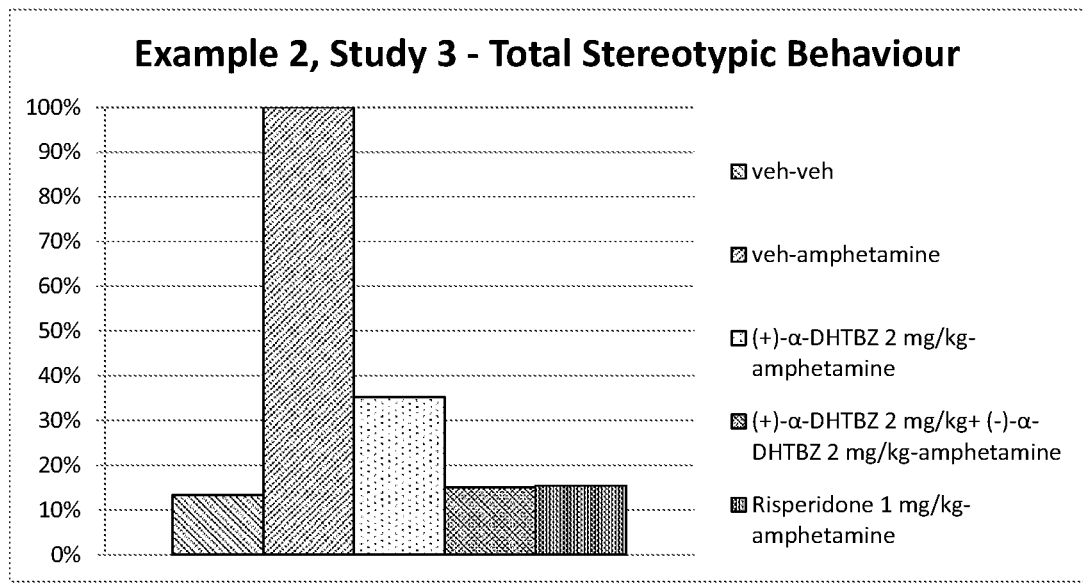
FIG. 6 shows the average total stereotypic behaviour by rats when treated with vehicle (with or without amphetamine induction) and (−)-α-dihydrotetrabenazine at a dose of 2 mg/kg, a combination of (+)-α-dihydrotetrabenazine at a dose of 2 mg/kg and (−)-α-dihydrotetrabenazine at a dose of 2 mg/kg, and risperidone at a dose of 1 mg/kg in amphetamine-induced rats, as described in Example 2, Study 3 below.

Rats dosed with either vehicle, (+)-α-DHTBZ 2 mg/kg, the combination of (−)-α-DHTBZ 2 mg/kg and (+)-α-DHTBZ 2 mg/kg or Risperidone 1 mg/kg were subjected to LMA testing first for 30 min and then for 60 minutes after vehicle or amphetamine challenge. Resulting stereotypic activity was evaluated in 3 min bins and as a total over the testing period. The normalised total stereotypic behaviour over the testing time is presented in FIG. 6.

When compared to vehicle-amphetamine group the vehicle-vehicle, (+)-α-DHTBZ 2 mg/kg, the combination of (−)-α-DHTBZ 2 mg/kg and (+)-α-DHTBZ 2 mg/kg and risperidone 1 mg/kg were significantly different.

Conclusions

This study evaluated the effect of compounds (+)-α-DHTBZ at a dose of 2 mg/kg, the combination of (+)-α-DHTBZ and (−)-α-DHTBZ at dose 2 mg/kg and risperidone at dose 1 mg/kg on amphetamine induced locomotor activity in male CD rats.

(+)-α-DHTBZ at the tested dose, the combination of (+)-α-DHTBZ and (−)-α-DHTBZ at doses 2 mg/kg and risperidone 1 mg/kg led to lower locomotor activity when compared to the vehicle-amphetamine group. (+)-α-DHTBZ at the tested dose, the combination of (+)-α-DHTBZ and (−)-α-DHTBZ at doses 2 mg/kg and risperidone 1 mg/kg led to reduced stereotypic behaviour when compared to the vehicle-amphetamine group.

Amphetamine induced locomotor activity was lesser in rats treated with the combination of (+)-α-DHTBZ and (−)-α-DHTBZ than in rats treated with (+)-α-DHTBZ only, despite it being shown that the (−)-α-isomer provides very little, if any, reduction induced locomotor activity.

STUDY 4

Animals were grouped as follows:
Group 1: 10 rats treated with Vehicle (t=0 min) and Vehicle (t=30 min)
Group 2: 10 rats treated with Vehicle (t=0 min) and Amphetamine (t=30 min)
Group 3: 10 rats treated with (+)-α-DHTBZ 0.5 mg/kg (t=0 min) and (−)-α-DHTBZ 0.5 mg/kg and Amphetamine (t=30 min)
Group 4: 10 rats treated with (+)-α-DHTBZ 1.0 mg/kg (t=0 min) and (−)-α-DHTBZ 0.5 mg/kg and Amphetamine (t=30 min)
Group 5: 10 rats treated with (+)-α-DHTBZ 1.0 mg/kg (t=0 min) and (−)-α-DHTBZ 1.0 mg/kg and Amphetamine (t=30 min)
Group 6: 10 rats treated with (+)-α-DHTBZ 1.5 mg/kg (t=0 min) and (−)-α-DHTBZ 1.0 mg/kg and Amphetamine (t=30 min)

Results

1 Distance Travelled

Figure 7:
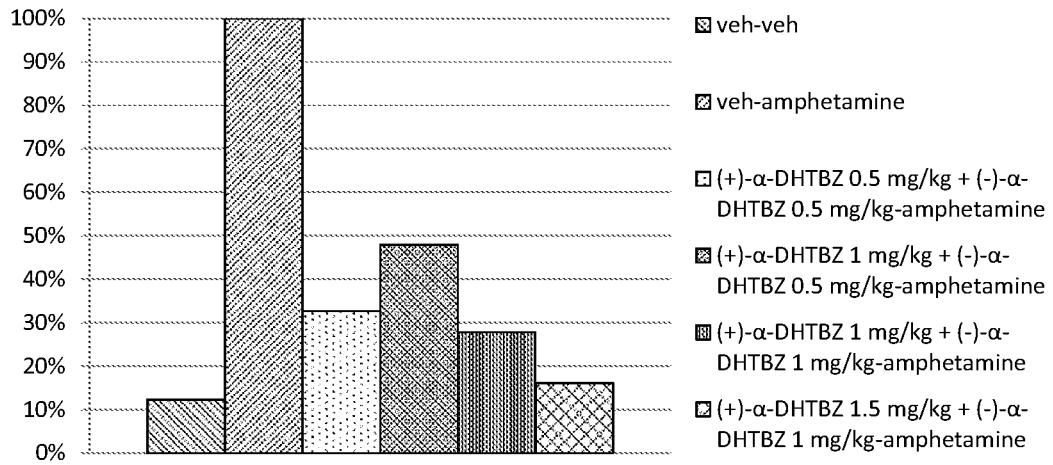
FIG. 7 shows the average total distance travelled by rats when treated with vehicle (with or without amphetamine induction) and combinations of (+)-α-dihydrotetrabenazine and (−)-α-dihydrotetrabenazine in varying ratios, and risperidone at a dose of 1 mg/kg in amphetamine-induced rats, as described in Example 2, Study 4 below.

Rats dosed with either vehicle, the combination of (+)-α-DHTBZ 0.5 mg/kg and (−)-α-DHTBZ 0.5 mg/kg, the combination of (+)-α-DHTBZ 1 mg/kg and (−)-α-DHTBZ 0.5 mg/kg, the combination of (+)-α-DHTBZ 1 mg/kg and (−)-α-DHTBZ 1 mg/kg or the combination of (+)-α-DHTBZ 1.5 mg/kg and (−)-α-DHTBZ 1 mg/kg were subjected to LMA testing first for 30 min and then for 60 minutes after vehicle or amphetamine challenge. Resulting locomotor activity was evaluated in 3 min bins and as a total over the testing period. The normalised total distance travelled over the testing time is presented in FIG. 7.

When compared to vehicle-amphetamine group the vehicle-vehicle, (+)-α-DHTBZ, the combination of (+)-α-DHTBZ 0.5 mg/kg and (−)-α-DHTBZ 0.5 mg/kg, the combination of (+)-α-DHTBZ 1 mg/kg and (−)-α-DHTBZ 0.5 mg/kg, the combination of (+)-α-DHTBZ 1 mg/kg and (−)-α-DHTBZ 1 mg/kg and the combination of (+)-α-DHTBZ 1.5 mg/kg and (−)-α-DHTBZ 1 mg/kg were significantly different.

Stereotypic Behaviour

Figure 8:
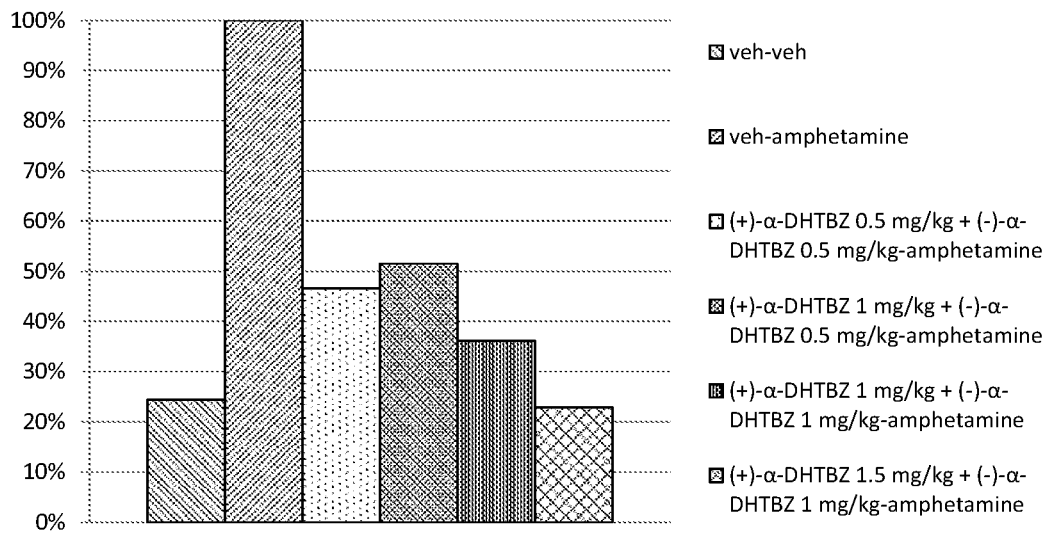
FIG. 8 shows the average total stereotypic behaviour by rats when treated with vehicle (with or without amphetamine induction) and combinations of (+)-α-dihydrotetrabenazine and (−)-α-dihydrotetrabenazine in varying ratios, and risperidone at a dose of 1 mg/kg in amphetamine-induced rats, as described in Example 2, Study 4 below.

Rats dosed with either vehicle, the combination of (+)-α-DHTBZ 0.5 mg/kg and (−)-α-DHTBZ 0.5 mg/kg, the combination of (+)-α-DHTBZ 1 mg/kg and (−)-α-DHTBZ 0.5 mg/kg, the combination of (+)-α-DHTBZ 1 mg/kg and (−)-α-DHTBZ 1 mg/kg or the combination of (+)-α-DHTBZ 1.5 mg/kg and (−)-α-DHTBZ 1 mg/kg were subjected to LMA testing first for 30 min and then for 60 minutes after vehicle or amphetamine challenge. Resulting stereotypic activity was evaluated in 3 min bins and as a total over the testing period. The normalised total stereotypic behaviour over the testing time is presented in FIG. 8.

When compared to the vehicle-vehicle group the combination of (+)-α-DHTBZ 1 mg/kg and (−)-α-DHTBZ 0.5 mg/kg was significantly different. When compared to vehicle-amphetamine group the vehicle-vehicle, the combination of (+)-α-DHTBZ 0.5 mg/kg and (−)-α-DHTBZ 0.5 mg/kg, the combination of (+)-α-DHTBZ 1 mg/kg and (−)-α-DHTBZ 0.5 mg/kg, the combination of (+)-α-DHTBZ 1 mg/kg and (−)-α-DHTBZ 1 mg/kg and the combination of (+)-α-DHTBZ 1.5 mg/kg and (−)-α-DHTBZ 1 mg/kg were significantly different.

Conclusions

This study evaluated the effect of the combination of (+)-α-DHTBZ and (−)-α-DHTBZ at doses 0.5 mg/kg+0.5 mg/kg, 1 mg/kg+0.5 mg/kg, 1 mg/kg+1 mg/kg and 1.5 mg/kg+1 mg/kg on amphetamine induced locomotor activity in male CD rats.

The combination of (+)-α-DHTBZ and (−)-α-DHTBZ at all the tested combinations and risperidone 1 mg/kg led to lower locomotor activity when compared to the vehicle-amphetamine group. The combination of (+)-α-DHTBZ and (−)-α-DHTBZ at all the tested doses and risperidone 1 mg/kg led to reduced stereotypic behaviour when compared to the vehicle-amphetamine group.

It would appear that there are interactions between the (+)-α-DHTBZ and (−)-α-DHTBZ affecting the ability of (+)-α-DHTBZ to block the amphetamine induced hyperactivity.

Comparing the data for rats dosed with a combination of (+)-α-DHTBZ at a dose of 1 mg/kg and (−)-α-DHTBZ at a dose of 0.5 mg/kg and rats dosed with a combination of (+)-α-DHTBZ at a dose of 1 mg/kg and (−)-α-DHTBZ at a dose of 1 mg/kg, given the demonstrated lack of efficiency of the (−)-α-isomer in isolation, it would not be expected that increases in the amount of (−)-α-isomer in the combination treatment would lead to a reduction in the locomotor activity in the tested rats.

Comments

Study 1 in Example 2 is consistent with the reported low activity of the (−)-α-isomer of tetrabenazine. Study 2 in Example 2 shows the efficacy of the (+)-α-isomer alone.

Study 3 in Example 2 demonstrates an unexpected improvement in the reduction of movement when a combination of (+)-α-dihydrotetrabenazine and (−)-α-dihydrotetrabenazine is administered compared with the results expected based on the administration of each isomer separately.

Study 4 in Example 2 demonstrates the reduction in movement following administration of combinations of (+)-α-dihydrotetrabenazine and (−)-α-dihydrotetrabenazine over a range of doses where both equal and non-equal amounts of both isomers are administered together.

Equivalents

It will readily be apparent that numerous modifications and alterations may be made to the specific embodiments of the invention described above without departing from the principles underlying the invention. All such modifications and alterations are intended to be embraced by this application.

The invention claimed is:

1. A pharmaceutical unit dosage form comprising a combination of (+)-α-dihydrotetrabenazine and (−)-α-dihydrotetrabenazine, or pharmaceutically acceptable salts thereof, and a pharmaceutically acceptable excipient, wherein the combination of (+)-α-dihydrotetrabenazine and (−)-α-dihydrotetrabenazine is a scalemic mixture, wherein the ratio of (+)-α-dihydrotetrabenazine to (−)-α-dihydrotetrabenazine is from 1.1:1 to 20:1.

2. A pharmaceutical unit dosage form according to claim 1, wherein the combination of (+)-α-dihydrotetrabenazine and (−)-α-dihydrotetrabenazine is unaccompanied by any other isomers of dihydrotetrabenazine.

3. A pharmaceutical unit dosage form according to claim 1 wherein the ratio of (+)-α-dihydrotetrabenazine to (−)-α-dihydrotetrabenazine is from 1.2:1 to 20:1.

4. A pharmaceutical unit dosage form according to claim 1, wherein the ratio of (+)-α-dihydrotetrabenazine to (−)-α-dihydrotetrabenazine is from 1.1:1 to 15:1.

5. A pharmaceutical unit dosage form according to claim 1, wherein the ratio of (+)-α-dihydrotetrabenazine to (−)-a-dihydrotetrabenazine is from 1.1:1 to 10:1.

6. A pharmaceutical unit dosage form according to claim 1, wherein the ratio of (+)-α-dihydrotetrabenazine to (−)-α-dihydrotetrabenazine is from 1.1:1 to 5:1.

7. A pharmaceutical unit dosage form according to claim 1, wherein the ratio of (+)-α-dihydrotetrabenazine to (−)-α-dihydrotetrabenazine is from 1.1:1 to 4:1.

8. A pharmaceutical unit dosage form according to claim 1, wherein the ratio of (+)-α-dihydrotetrabenazine to (−)-α-dihydrotetrabenazine is from 1.1:1 to 3:1.

9. A pharmaceutical unit dosage form according to claim 1, wherein the ratio of (+)-α-dihydrotetrabenazine to (−)-α-dihydrotetrabenazine is from 1.2:1 to 15:1.

10. A pharmaceutical unit dosage form according to claim 1, wherein the ratio of (+)-α-dihydrotetrabenazine to (−)-α-dihydrotetrabenazine is from 1.2:1 to 10:1.

11. A pharmaceutical unit dosage form according to claim 1, wherein the ratio of (+)-α-dihydrotetrabenazine to (−)-α-dihydrotetrabenazine is from 1.2:1 to 5:1.

12. A pharmaceutical unit dosage form according to claim 1, wherein the ratio of (+)-α-dihydrotetrabenazine to (−)-α-dihydrotetrabenazine is from 1.2:1 to 4:1.

13. A pharmaceutical unit dosage form according to claim 1, wherein the ratio of (+)-α-dihydrotetrabenazine to (−)-α-dihydrotetrabenazine is from 1.2:1 to 3:1.

14. A method of treating a movement disorder in a subject in need thereof, the method comprising administering to the subject the pharmaceutical unit dosage form according to claim 1.

15. A method according to claim 14, wherein the method comprises administering to a subject in need thereof an effective therapeutic amount of the pharmaceutical unit dosage form sufficient to provide a dosage of from 1 mg to 20 mg of (+)-α-dihydrotetrabenazine per day.

16. A method according to claim 14, wherein the method comprises administering to a subject an amount of the pharmaceutical unit dosage form of from 0.01 mg/kg to 0.3 mg/kg per day provided that the total amount of (+)-α-dihydrotetrabenazine administered per day is in the range from 1 mg to 20 mg.

17. A method according to claim 14, wherein the movement disorder is a hyperkinetic movement disorder selected from Huntington's disease, hemiballismus, senile chorea, tic disorders, tardive dyskinesia, dystonia and Tourette's syndrome.

18. A method according to claim 14, wherein the movement disorder is Tourette's syndrome.

19. A method according to claim 14, wherein the method comprises administering to a subject an amount of the pharmaceutical unit dosage form sufficient to cause a level of blocking of from 20% to 90% of VMAT2 proteins in the subject.

20. A method according to claim 14, wherein the combination of (+)-α-dihydrotetrabenazine and (−)-α-dihydrotetrabenazine is unaccompanied by any other isomers of dihydrotetrabenazine.

21. A method according to claim 14, wherein the subject is a human subject.

* * * * *